US008846749B2

(12) United States Patent
Na et al.

(10) Patent No.: US 8,846,749 B2
(45) Date of Patent: Sep. 30, 2014

(54) ANTICANCER-AIDING COMPOUND, METHOD FOR PREPARING THE SAME, ANTICANCER-AIDING COMPOSITION CONTAINING THE SAME AND METHOD FOR REDUCING ANTICANCER DRUG RESISTANCE USING THE SAME

(75) Inventors: Young Hwa Na, Daegu (KR); Young Joo Kwon, Goyang-si (KR); Hwa Jeong Lee, Seoul (KR); Song Wha Chae, Seoul (KR); Sang Wook Woo, Yeongi-gun (KR); Hee Ju Cho, Daegu (KR)

(73) Assignee: Ewha University-Industry Collaboration Foundation, Seoul (KR)

( * ) Notice: Subject to any disclaimer, the term of this patent is extended or adjusted under 35 U.S.C. 154(b) by 186 days.

(21) Appl. No.: 13/375,217

(22) PCT Filed: Aug. 19, 2010

(86) PCT No.: PCT/KR2010/005492
§ 371 (c)(1),
(2), (4) Date: Apr. 10, 2012

(87) PCT Pub. No.: WO2011/021864
PCT Pub. Date: Feb. 24, 2011

(65) Prior Publication Data
US 2012/0190724 A1 Jul. 26, 2012

(30) Foreign Application Priority Data
Aug. 21, 2009 (KR) ........................ 10-2009-0077786

(51) Int. Cl.
*A61K 31/382* (2006.01)
*C07D 335/16* (2006.01)
*C07D 407/14* (2006.01)
*C07D 335/04* (2006.01)
*C07D 409/14* (2006.01)
*C07D 409/12* (2006.01)
*C07D 407/12* (2006.01)
*C07D 311/78* (2006.01)
*C07D 311/92* (2006.01)

(52) U.S. Cl.
CPC ............ *C07D 409/14* (2013.01); *C07D 407/14* (2013.01); *C07D 335/04* (2013.01); *C07D 409/12* (2013.01); *C07D 407/12* (2013.01); *C07D 311/78* (2013.01); *A61K 31/382* (2013.01); *C07D 335/16* (2013.01); *C07D 311/92* (2013.01)
USPC .............................. 514/437; 549/27; 549/391

(58) Field of Classification Search
CPC ................................ A61K 31/382; C07D 335/16
USPC ...................... 541/437; 549/391, 27; 514/437
See application file for complete search history.

(56) References Cited

U.S. PATENT DOCUMENTS 5,292,744 A   3/1994   Sasse et al.

FOREIGN PATENT DOCUMENTS

EP   2 050 745 A1   4/2009
WO   93/07138 A1    4/1993

OTHER PUBLICATIONS

King, Med. Chem., Principle and Practice (1994), pp. 206-208.*
Chen et al., "Xanthonolol: a calcium channel and beta-adrenoceptor blocker with vasodilating properties," *General Pharmacology* 24(6):1425-1433, 1993.
Chieli et al., "Effects of flavonols on P-glycoprotein activity in cultured rat hepatocytes," *Life Sciences* 57(19):1741-1751, 1995.
Chung et al., "Modulation of P-glycoprotein-Mediated Resistance by Kaempferol Derviatives Isolated from *Zingiber zerumbet*," *Phytotherapy Research* 21:565-569, 2007.
Chung et al., "Potent Modulation of P-glycoprotein Activity by Naturally Occuring Phenylbutenoids from *Zingiber cassumunar*," *Phytotherapy Research* 23:472-476, 2009.
Critchfield et al., "Modulation of Adriamycin® accumulation and efflux by flavonoids in HCT-15 colon cells," *Biochemical Pharmacology* 48(7):1437-1445, 1994.
Endicott et al., "The biochemistry of P-glycoprotein-mediated multidrug resistance," *Annual Review of Biochemistry* 58:137-171, 1989.
Fromm, "P-glyocoprotein: a defense mechanism limiting oral bioavailability and CNS accumulation of drugs," *International Journal of Clinical Pharmacology and Therapeutics* 38(2):69-74, 2000.
Fuqua et al., "P-Glycoprotein Expression in Human Breast Cancer Cells," *Cancer Research* 47:2103-2106, Apr. 15, 1987.
Gottesman et al., "Biochemistry of multidrug resistance mediated by the multidrug transporter," *Annual Review of Biochemistry* 62:385-427, 1993.
Hambloch et al., "QSAR with the tuberculostatic activity of polyhydroxy xanthones and their $^{13}$C-NMR chemical shifts," *European Journal of Medicinal Chemistry* 20(1):71-77, 1985.
Ikegawa et al., "Inhibition of P-glycoprotein by flavonoid derivatives in adriamycin-resistant human myelogenous leukemia (K562/ADM) cells," *Cancer Letters* 177:89-93, 2002.
Juranka et al., "P-glycoprotein: multidrug-resistance and a superfamily of membrane-associated transport proteins," *The FASEB Journal* 3(14):2583-2592, 1989.
Klohs et al. "Possible Link between the Intrinsic Drug Resistance of Colon Tumors and a Detoxification Mechanism of Intestinal Cells," *Cancer Research* 48:3025-3030, Jun. 1, 1988.

(Continued)

Primary Examiner — Taofiq A Solola
(74) Attorney, Agent, or Firm — Seed IP Law Group PLLC

(57) ABSTRACT

The present invention provides a novel xanthone derivative compound or a pharmaceutically acceptable salt thereof. The compound is useful as a chemosensitizer that reduces anticancer drug resistance.

1 Claim, No Drawings

(56) References Cited

OTHER PUBLICATIONS

Lin et al., "Synthesis and Anti-inflammatory Effects of Xanthone Derivatives," *Journal of Pharmacy and Pharmacology 48*:532-538, 1996.

Lum et al., "MDR expression in normal tissues: pharmacological implications for the clinical use of P-glycoprotein inhibitors," *Hematology/Oncology Clinics of North America 9*(2):319-336, Apr. 1995.

Marona et al., "Aminoalkanolic derivatives of xanthone with potential antiepileptic activity," *Pharmazie 53*:219-223, 1998.

Phang et al., "Flavonol-stimulated Efflux of 7,12-Dimethylbenz(a)anthracene in Multidrug-resistant Breast Cancer Cells," *Cancer Research 53*(24):5977-5981, Dec. 15, 1993.

Potter, "Cancer prevention: epidemiology and experiment," *Cancer Letters 114*:7-9, 1997.

Rewcastle et al., "Potential Antitumor Agents. 58. Synthesis and Structure-Activity Relationships of Substituted Xanthenone-4-acetic Acids Active against the Colon 38 Tumor in Vivo," *Journal of Medicinal Chemistry 32*(4):793-799, 1989.

Scambia et al., "Quercetin potentiates the effect of Adriamycin in a multidrug-resistant MCF-7 human breast-cancer cell line: P-glycoprotein as a possible target," *Cancer Chemotherapy and Pharmacology 34*:459-464, 1994.

Talalay et al., "Chemoprotection against cancer by isothiocyanates and glucosinolates," *Biochemical Society Transactions 24*:806-810, 1996.

Theibaut et al., "Cellular localization of the multidrug-resistance gene product P-glycoprotein in normal human tissues," *Proceedings of the National Academy of Sciences 84*:7735-7738, Nov. 1987.

Wang et al., "Antihypertensive and Vasorelaxing Activities of Synthetic Xanthone Derivatives," *Bioorganic & Medicinal Chemistry 10*:567-572, 2002.

Wargovich, "Experimental evidence for cancer preventive elements in foods," *Cancer Letters 114*:11-17, 1997.

Woo et al., "Synthesis of new xanthone analogues and their biological activity test—Cytotoxicity, topoisomerase II inhibition, and DNA cross-linking study," *Bioorganic & Medicinal Chemistry Letters 17*:1163-1166, 2007.

Woo et al., "Synthesis, Cytotoxicity and Topoisomerase II Inhibition Study of New Thioxanthone Analogues," *Bulletin of the Korean Chemical Society 29*(2):471-474, 2008.

Yeh et al., "A New Functional Role for P-Glycoprotein: Efflux Pump for Benzo(a)pyrene in Human Breast Cancer MCF-7 Cells," *Cancer Research 52*(23):6692-6695, Dec. 1, 1992.

Zhang et al., "Anticarcinogenic Activities of Organic Isothiocyanates: Chemistry and Mechanisms," *Cancer Research (Suppl) 54*:1976s-1981s, Apr. 1, 1994.

Zhou et al., "Herbal Modulation of P-Glycoprotein," *Drug Metabolism Reviews 36*(1):57-104, 2004.

\* cited by examiner

ANTICANCER-AIDING COMPOUND, METHOD FOR PREPARING THE SAME, ANTICANCER-AIDING COMPOSITION CONTAINING THE SAME AND METHOD FOR REDUCING ANTICANCER DRUG RESISTANCE USING THE SAME

TECHNICAL FIELD

The present invention relates to an anticancer-aiding compound, a method for preparing the same, an anticancer-aiding composition containing the same and a method for reducing anticancer drug resistance using the same.

BACKGROUND ART

The main cause for therapeutic failure of cancer in a human is multidrug resistance (MDR) which refers to development of resistance of cancer cells to anticancer drugs entirely different in terms of structure or mechanism and is closely connected with the overexpression of a transport protein known as P-glycoprotein (P-gp). P-gp is an ATP-dependent transport protein involved in cellular efflux of a wide variety of fat-soluble substances including anticancer drugs. P-gp lowers a concentration of a therapeutic drug in cancer cells, resulting in increased drug resistance of the cancer cells (Juranka et al., *FASEB J.*, 3, pp 2583-2592, 1989; Fuqua et al., *Cancer Res.*, 47, pp 2103-2106, 1987; Endicott et al., *Ann. Rev. Biochem.*, 58, pp 137-171, 1989; and Gottesman et al., *Ann. Rev. Biochem*, 62, pp 385-427, 1993). Further, it is known that P-gp is also present in diverse normal organs such as liver, small intestines, kidney and brain and serves a cellular defense function by cellular efflux of toxic substances introduced to the living body (Theibaut et al., *Proc. Natl. Acad. Sci.*, 84, pp 7735-7738, 1987; Lum et al., *Hematol. Oncol. Clin. North Am.*, 9 pp 319-336, 1995; M. F. Fromm, *Int. J. Clin. Pharmacol. Ther.*, 38, pp 69-74, 2000; and Stenkampf et al., *Cancer Res.*, 48 pp 3025-3030, 1988).

Meanwhile, it is currently known that high intake of fruits or vegetables leads to a decrease in risk of carcinogenesis (J. D. Potter, *Cancer Lett.*, 114, pp 7-9, 1997; and M. J. Wargovich, *Cancer Lett.*, 114, pp 11-17, 1997). There has been reported that a diversity of ingredients derived from natural substances is implicated in modulation of the activity of P-gp in in vitro human cancer cells and in vivo animal models (Scambia et al., *Cancer Chemother. Pharmacol.*, 34, pp 459-464, 1994; Chieli et al., *Life Sci.*, pp 1741-1751, 1995; Ikegawa et al., *Cancer lett.*, 177, pp 89-93, 2002; Zhou et al., *Drug Metab Rev*, 36 pp 57-104, 2004; Chung et al., *Phytother Res*, 21, pp 565-569, 2007; and Chung et al., *Phytother Res*, 23, pp 472-476, 2009). Further, there has been reported that flavonoids have an effect on P-gp-induced efflux of dimethylbenz[α]anthracene, benzo[α]pyrene and adriamycin (Yeh et al., *Cancer Res.*, 52, pp 6692-6695, 1992; Phang et al., *Cancer Res.*, 53, pp 5977-5981, 1993; and Critchfield et al., *Biochem. Pharmacol.*, 48, pp 1437-1445, 1994). There has also been reported that organic isothiocyanates found in a variety of edible plants suppress the formation of chemical carcinogens in animal models to thereby prevent carcinogenesis (Talalay et al., *Biochem. Soc. Trans.*, 24, pp 806-810, 1996; and Zhang et al., *Cancer Res.* (suppl), 54, pp 1976-1981, 1994).

Compounds of the present invention are a xanthone compound having structural connection with anthraquinone and may be obtained in a relatively abundant amount from the fruit skin, tree bark or dried latex of guttiferaeous plants such as mangosteen (*Garcinia mangostana* L.). It is known that xanthone compounds have an anticancer action (G. W. Rewcastle et al., *J. Med. Chem.* 32, pp 793-799. 1989), an anti-inflammatory action (C. N. Lin et al., *J. Pharm. Pharmacol.* 48 pp 532-538, 1996), an antibacterial action (H. Hambloch et al., *Eur. J. Med. Chem.* 20, pp 71-77. 1985) and other pharmacological actions (H. Marona et al., *Pharmazie*, 53, pp 219-223, 1998; I. J. Chen et al., *Gen. Pharmacol*, 24, pp 1425-1433, 1993; and L. W. Wang et al., *Bioorg. Med. Chem.*, 10, pp 567-572, 2002), depending on the position of a xanthone ring.

However, despite continued research on substances isolated from mangosteen, there has been no teaching or suggestion regarding uses of xanthone structural derivatives as a chemosensitizer which specifically acts on cancer cells having resistance to conventional anticancer drugs by exhibiting an inhibitory action against the P-gp activity.

DISCLOSURE OF THE INVENTION

Technical Problem

Therefore, the present invention is intended to provide an anticancer-aiding substance that decreases anticancer drug resistance by specifically acting on cancer cells having resistance to conventional anticancer drugs, and preferably a novel xanthone derivative or a pharmaceutically acceptable salt thereof that can be used as a chemosensitizer.

Further, the present invention is intended to provide a method for preparing a novel xanthone derivative or a pharmaceutically acceptable salt thereof.

Further, the present invention is intended to provide an anticancer-aiding pharmaceutical composition containing at least one of a novel xanthone derivative and a pharmaceutically acceptable salt thereof.

Further, the present invention is intended to provide a use of a novel xanthone derivative or a pharmaceutically acceptable salt thereof for decreasing anticancer drug resistance.

Further, the present invention is intended to provide a method for reducing anticancer drug resistance, including administering at least one of a novel xanthone derivative and a pharmaceutically acceptable salt thereof to a subject.

Further, the present invention is intended to provide a method for reducing resistance of cancer cells to an anticancer drug, including contacting the cancer cells with at least one of a novel xanthone derivative and a pharmaceutically acceptable salt thereof.

Technical Solution

The present invention provides a compound represented by formula I or a pharmaceutically acceptable salt thereof:

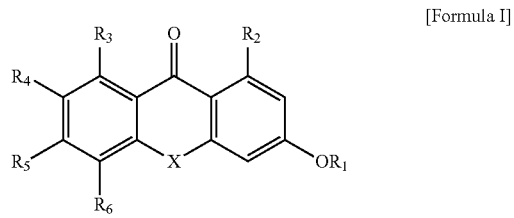

[Formula I]

wherein X represents S or O;

$R_1$ represents —$CH_2$—CH(OH)—$CH_2Cl$, —$CH_2$—CH(OH)—$CH_2OH$, —$CH_2$—CH(SH)—$CH_2Cl$, —$CH_2$—CH(SH)—$CH_2OH$,

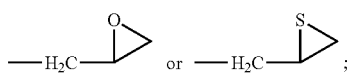

$R_2$ represents hydrogen, —OH, $(C_1$-$C_4)$alkoxy,

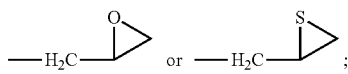

and $R_3$, $R_4$, $R_5$, and $R_6$ each independently represent H or $(C_1$-$C_4)$alkoxy, or alternatively $R_3$ and $R_4$, $R_4$ and $R_5$, and $R_5$ and $R_6$ represent —CH=CH—CH=CH—; provided that when $R_2$ represents —OH and $R_3$ to $R_6$ represent hydrogen, $R_1$ is not —CH$_2$—CH(OH)—CH$_2$Cl, —CH$_2$—CH(SH)—CH$_2$Cl or

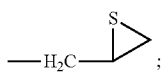

and when $R_2$ represents OH, $R_3$ to $R_5$ represent H and $R_6$ represents methoxy, $R_1$ is not —CH$_2$—CH(OH)—CH$_2$Cl.

In the present invention, the compound represented by formula I or the pharmaceutically acceptable salt thereof is preferably as follows:
1-hydroxy-5-methoxy-3-(thiiran-2-ylmethoxy)-9H-xanthen-9-one;
1,3-bis(thiiran-2-ylmethoxy)-9H-xanthen-9-one;
1,3-bis(thiiran-2-ylmethoxy)-5-methoxy-9H-xanthen-9-one;
3-(2,3-dihydroxypropoxy)-1-hydroxy-9H-xanthen-9-one;
3-(2,3-dihydroxypropoxy)-1-hydroxy-5-methoxy-9H-xanthen-9-one;
3-(3-chloro-2-hydroxypropoxy)-1-methoxy-9H-xanthen-9-one;
8,10-bis(thiiran-2-ylmethoxy)-7H-benzo[c]xanthen-7-one;
3-(3-chloro-2-mercaptopropoxy)-1-hydroxy-5-methoxy-9H-xanthen-9-one;
11-hydroxy-9-(thiiran-2-ylmethoxy)-12H-benzo[a]xanthen-12-one;
9,11-bis(thiiran-2-ylmethoxy)-12H-benzo[a]xanthen-12-one;
11-hydroxy-9-(oxiran-2-ylmethoxy)-12H-benzo[a]xanthen-12-one;
9,11-bis(oxiran-2-ylmethoxy)-12H-benzo[a]xanthen-12-one;
1-hydroxy-3-(thiiran-2-ylmethoxy)-12H-benzo[b]xanthen-12-one;
1,3-bis(thiiran-2-ylmethoxy)-12H-benzo[b]xanthen-12-one;
1-hydroxy-3-(oxiran-2-ylmethoxy)-12H-benzo[b]xanthen-12-one;
1,3-bis(oxiran-2-ylmethoxy)-12H-benzo[b]xanthen-12-one;
and pharmaceutically acceptable salts thereof.

The compound represented by formula I in accordance with the present invention is more preferably 8,10-bis(thiiran-2-ylmethoxy)-7H-benzo[c]xanthen-7-one, 1,3-bis(thiiran-2-ylmethoxy)-12H-benzo[b]xanthen-12-one or a pharmaceutically acceptable salt thereof.

As used herein, the term "pharmaceutically acceptable salt" refers to a salt commonly used in the pharmaceutical industry, and examples thereof include a salt with an inorganic ion such as calcium, potassium, sodium, or magnesium; a salt with an inorganic acid such as hydrochloric acid, nitric acid, phosphoric acid, bromic acid, iodic acid, perchloric acid, tartaric acid, or sulfuric acid; a salt with an organic acid such as methanesulfonic acid, ethanesulfonic acid, benzenesulfonic acid, p-toluenesulfonic acid, naphthalene sulfonic acid, acetic acid, trifluoroacetic acid, citric acid, maleic acid, succinic acid, oxalic acid, benzoic acid, tartaric acid, fumaric acid, mandelic acid, propionic acid, citric acid, lactic acid, glycolic acid, gluconic acid, galacturonic acid, glutamic acid, glutaric acid, glucuronic acid, aspartic acid, ascorbic acid, carbonic acid, vanillic acid, or hydroiodic acid; a salt with a sulfonic acid such as methanesulfonic acid, ethanesulfonic acid, benzenesulfonic acid, p-toluenesulfonic acid, or naphthalene sulfonic acid; a salt with an amino acid such as glycine, arginine, or lysine; and a salt with an amine such as trimethylamine, triethylamine, ammonia, pyridine, or picoline. However, the present invention is not limited thereto.

Further, the present invention provides a method for preparing a compound represented by formula I-1, including reacting a compound of formula II with epichlorohydrin or epithiochlorohydrin in the presence of a base:

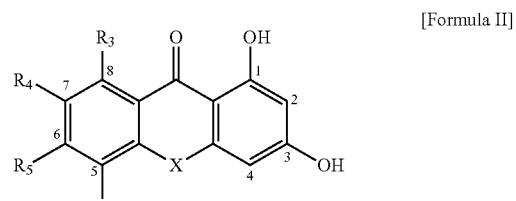

[Formula II]

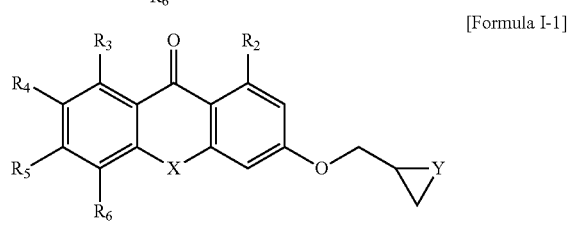

[Formula I-1]

wherein X and Y each independently represent —S— or —O—;

$R_2$ represents —OH,

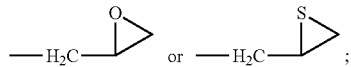

and $R_3$, $R_4$, $R_5$, and $R_6$ each independently represent H or $(C_1$-$C_4)$alkoxy, or alternatively $R_3$ and $R_4$, $R_4$ and $R_5$, and $R_5$ and $R_6$ represent —CH=CH—CH=CH—; provided that when $R_2$ represents —OH and $R_3$ to $R_6$ represent hydrogen, Y is not S.

In the method for preparing a compound represented by formula I-1 in accordance with the present invention, the compound represented by formula II, which is a starting material, is commercially available or may be prepared by a known method (M. K. Rao et al., *Bull. Chem. Soc. Jap.*, 47, pp 2059-2060, 1974). For example, for a compound of formula II in which $R_3$ and $R_4$, $R_4$ and $R_5$, and $R_5$ and $R_6$ represent —CH=CH—CH=CH—, the compound is synthesized by ☐ a method of mixing known 3-hydroxy-2-naphthoic acid with phloroglucinol, ZnCl$_2$ and POCl$_3$, followed by stirring under reflux, ☐ a method of mixing 2,4,6-trihydroxybenzoic acid and 2-naphthol with ZnCl$_2$ and POCl$_3$, followed by stirring under reflux, or □ a method of mixing 1-hydroxy-2-naphthoic acid, phloroglucinol, $P_2O_5$ and methyl hydrogen sulfate.

In the method for preparing a compound represented by formula I-1 in accordance with the present invention, the base is preferably selected from $K_2CO_3$, $CS_2CO_3$, NaOH and NaH. When only —OH at the 3-position of xanthone or thioxanthone is substituted, $K_2CO_3$ is preferably used, and when all of —OH at the 1- and 3-positions of xanthone or thioxanthone are substituted, $CS_2CO_3$ is preferably used. Here, the amount of the base used is preferably in a range of about 1.5 to 3 molar equivalents, and more preferably 2 molar equivalents, relative to the molar equivalent of the compound represented by formula II which is used as a starting material.

In the method for preparing a compound represented by formula I-1 in accordance with the present invention, a reaction solvent is preferably a conventional organic solvent such as acetone or dimethylformamide (DMF), more preferably an anhydrous solvent thereof, and even more preferably anhydrous acetone.

In the method for preparing a compound represented by formula I-1 in accordance with the present invention, a reaction temperature is preferably a reflux temperature, and the reaction time is preferably in a range of 4 hours to 24 hours. The reaction time may vary depending on the reaction temperature. When the reaction solvent is acetone and the reaction is carried out at the reflux temperature, the reaction time is preferably about 6 hours.

Further, the present invention provides a method for preparing a compound represented by formula I-2, including 1) a step of reacting a compound represented by formula II with epichlorohydrin or epithiochlorohydrin in the presence of a weak base to prepare a compound represented by formula I-1, and 2) a step of converting the compound represented by formula I-1 into a compound represented by formula I-2 in the presence of an acid:

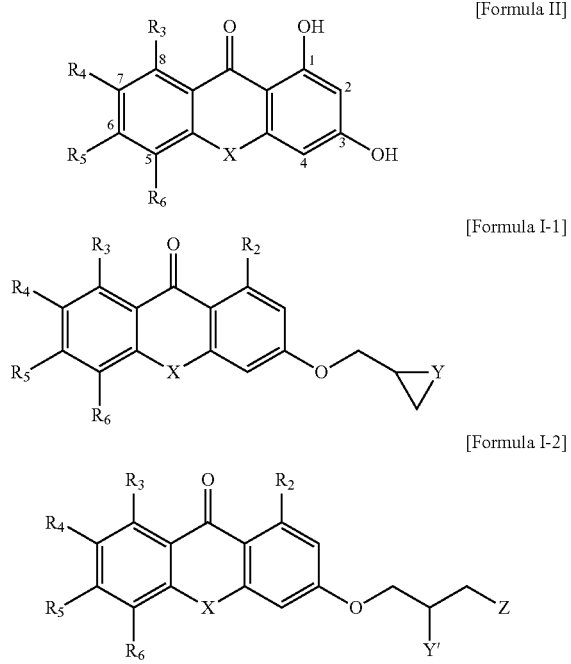

wherein X and Y each independently represent —S— or —O—;

Y' represents —OH or —SH;

Z represents —OH or —Cl;

$R_2$ represents —OH; and $R_3$, $R_4$, $R_5$, and $R_6$ each independently represent H or $(C_1$-$C_4)$alkoxy, or alternatively $R_3$ and $R_4$, $R_4$ and $R_5$, and $R_5$ and $R_6$ represent —CH═CH—CH═CH—; provided that when $R_2$ represents —OH, and $R_3$ to $R_6$ represent hydrogen, Y is not —S— and Y' is not —SH or —OH; when $R_2$ represents —OH, and $R_3$ to $R_6$ represent hydrogen, Y' is not —OH and Z is not —Cl, and when $R_2$ represents —OH, $R_3$ to $R_5$ represent hydrogen, and $R_6$ represents a methoxy group, Y' represents —OH and Z is not —Cl.

In Step 1) of the method for preparing the compound represented by formula I-2 in accordance with the present invention, examples of the weak base include $K_2CO_3$, $Na_2CO_3$, and $CaCO_3$, and the equivalent of the base used, a reaction temperature, a reaction time, and a reaction solvent are as described in the method for preparing a compound represented by formula I-1 in accordance with the present invention.

In Step 2) of the method for preparing the compound represented by formula I-2 in accordance with the present invention, the acid is preferably hydrochloric acid, trifluoroacetic acid or trichloroacetic acid. For the compound of formula I-2, when Z represents —Cl, the acid is preferably hydrochloric acid. For the compound of formula I-2, when Z represents OH, the acid is preferably trichloroacetic acid. Here, the equivalent of the acid used is preferably in a range of 5 to 20 equivalents relative to the equivalent of the compound represented by formula I-1.

In Step 2) of the method for preparing a compound represented by formula I-2 in accordance with the present invention, the reaction temperature is preferably in a range of about 0 to about 60° C. When the acid is hydrochloric acid, the reaction temperature is more preferably in a range of 15 to 30° C., and when the acid is trichloroacetic acid, the reaction temperature is more preferably in a range of about 45 to about 55° C.

In Step 2) of the method for preparing the compound represented by formula I-2 in accordance with the present invention, the reaction solvent is preferably a mixture of ethyl acetate and water.

Further, the present invention provides an anticancer-aiding pharmaceutical composition containing at least one of a compound represented by formula I and a pharmaceutically acceptable salt thereof:

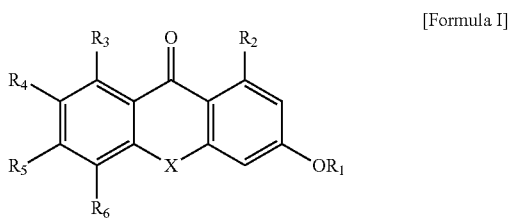

wherein X represents —S— or —O—;

$R_1$ represents —$CH_2$—CH(OH)—$CH_2$Cl, —$CH_2$—CH(OH)—$CH_2$OH, —$CH_2$—CH(SH)—$CH_2$Cl, —$CH_2$—CH(SH)—$CH_2$OH,

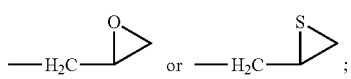

$R_2$ represents hydrogen, —OH, $(C_1$-$C_4)$alkoxy,

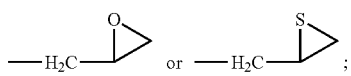

and $R_3$, $R_4$, $R_5$, and $R_6$ each independently represent H or $(C_1$-$C_4)$alkoxy, or alternatively $R_3$ and $R_4$, $R_4$ and $R_5$, and $R_5$ and $R_6$ represent —CH=CH—CH=CH—.

In the anticancer-aiding composition of the present invention, a compound represented by formula I or a pharmaceutically acceptable salt thereof is preferably selected from the following compounds:
3-(3-chloro-2-hydroxypropoxy)-1-hydroxy-5-methoxy-9H-xanthen-9-one;
3-(3-chloro-2-hydroxypropoxy)-1-hydroxy-9H-xanthen-9-one;
1-hydroxy-5-methoxy-3-(thiiran-2-ylmethoxy)-9H-xanthen-9-one;
1,3-bis(thiiran-2-ylmethoxy)-9H-xanthen-9-one;
1,3-bis(thiiran-2-ylmethoxy)-5-methoxy-9H-xanthen-9-one;
3-(2,3-dihydroxypropoxy)-1-hydroxy-9H-xanthen-9-one;
3-(2,3-dihydroxypropoxy)-1-hydroxy-5-methoxy-9H-xanthen-9-one;
1-hydroxy-3-(thiiran-2-ylmethoxy)-9H-thioxanthen-9-one;
3-(3-chloro-2-hydroxypropoxy)-1-methoxy-9H-xanthen-9-one;
3-(3-chloro-2-hydroxypropoxy)-1-hydroxy-9H-thioxanthen-9-one;
3-(3-chloro-2-mercaptopropoxy)-1-hydroxy-9H-thioxanthen-9-one;
8,10-bis(thiiran-2-ylmethoxy)-7H-benzo[c]xanthen-7-one;
3-(3-chloro-2-mercaptopropoxy)-1-hydroxy-5-methoxy-9H-xanthen-9-one;
11-hydroxy-9-(thiiran-2-ylmethoxy)-12H-benzo[a]xanthen-12-one;
9,11-bis(thiiran-2-ylmethoxy)-12H-benzo[a]xanthen-12-one;
11-hydroxy-9-(oxiran-2-ylmethoxy)-12H-benzo[a]xanthen-12-one;
9,11-bis(oxiran-2-ylmethoxy)-12H-benzo[a]xanthen-12-one;
1-hydroxy-3-(thiiran-2-ylmethoxy)-12H-benzo[b]xanthen-12-one;
1,3-bis(thiiran-2-ylmethoxy)-12H-benzo[b]xanthen-12-one;
1-hydroxy-3-(oxiran-2-ylmethoxy)-12H-benzo[b]xanthen-12-one;
1,3-bis(oxiran-2-ylmethoxy)-12H-benzo[b]xanthen-12-one; and
pharmaceutically acceptable salts thereof.

In the composition of the present invention, the compound represented by formula I or the pharmaceutically acceptable salt thereof is more preferably 3-(3-chloro-2-hydroxypropoxy)-1-hydroxy-9H-thioxanthen-9-one, 8,10-bis(thiiran-2-ylmethoxy)-7H-benzo[c]xanthen-7-one, 1,3-bis(thiiran-2-ylmethoxy)-12H-benzo[b]xanthen-12-one or the pharmaceutically acceptable salt thereof.

As used herein, the term "anticancer-aiding" means increasing the effect of an anticancer drug, or decreasing resistance to an anticancer drug. The pharmaceutical composition of the present invention is more preferably a chemosensitizer which is capable of reducing anticancer drug resistance.

In the anticancer-aiding pharmaceutical composition of the present invention, the anticancer drug is a substance which serves as a substrate for P-gp, and examples thereof include daunomycin, doxorubicin, vinblastine, vincristine, etoposide, paclitaxel, docetaxel, and irinotecan. The present invention is not limited thereto.

The pharmaceutical composition of the present invention may contain additives, such as a diluent, a binder, a disintegrant, a lubricant, a pH-adjusting agent, an antioxidant and a solubilizer, which are pharmaceutically acceptable, within the range where effects of the present invention are not impaired.

The diluent may include sugar, starch, microcrystalline cellulose, lactose (lactose hydrate), glucose, D-mannitol, alginate, an alkaline earth metal salt, clay, polyethylene glycol, anhydrous dibasic calcium phosphate, and a mixture thereof; The binder may include starch, microcrystalline cellulose, highly dispersive silica, mannitol, D-mannitol, sucrose, lactose hydrate, polyethylene glycol, polyvinylpyrrolidone (povidone), a polyvinylpyrrolidone copolymer (copovidone), hypromellose, hydroxypropylcellulose, natural gum, synthetic gum, copovidone, gelatin, and a mixture thereof.

The disintegrant may include starches or modified starches such as sodium starch glycolate, corn starch, potato starch, and pregelatinized starch; clays such as bentonite, montmorillonite, and veegum; celluloses such as microcrystalline cellulose, hydroxypropylcellulose, and carboxymethylcellulose; algins such as sodium alginate, and alginic acid; crosslinked celluloses such as croscarmellose sodium; gums such as guar gum, and xanthan gum; crosslinked polymers such as crosslinked polyvinylpyrrolidone (crospovidone); effervescent agents such as sodium bicarbonate and citric acid, and mixtures thereof.

The lubricant may include talc, stearic acid, magnesium stearate, calcium stearate, sodium lauryl sulfate, hydrogenated vegetable oil, sodium benzoate, sodium stearyl fumarate, glyceryl behenate, glyceryl monolaurate, glyceryl monostearate, glyceryl palmitostearate, colloidal silicon dioxide, and mixtures thereof.

The pH-adjusting agent may include acidifying agents such as acetic acid, adipic acid, ascorbic acid, sodium ascorbate, sodium etherate, malic acid, succinic acid, tartaric acid, fumaric acid, and citric acid, and basifying agents such as precipitated calcium carbonate, aqueous ammonia, meglumine, sodium carbonate, magnesium oxide, magnesium carbonate, sodium citrate, and tribasic calcium phosphate.

The antioxidant may include dibutyl hydroxy toluene, butylated hydroxyanisole, tocopherol acetate, tocopherol, propyl gallate, sodium hydrogen sulfite, and sodium pyrosulfite.

The solubilizer may include sodium lauryl sulfate, polyoxyethylene sorbitan fatty acid ester (such as polysorbate), docusate sodium and poloxamer.

In order to prepare a delayed-release formulation, the pharmaceutical composition of the present invention may contain an enteric polymer, a water-insoluble polymer, a hydrophobic compound, and a hydrophilic polymer.

The enteric polymer refers to a polymer which is insoluble or stable under acidic conditions of less than pH 5 and is dissolved or degraded under specific pH conditions of pH 5 or higher. Examples of the enteric polymer include enteric cellulose derivatives such as hypromellose acetate succinate, hypromellose phthalate (hydroxypropylmethylcellulose phthalate), hydroxymethylethylcellulose phthalate, cellulose acetate phthalate, cellulose acetate succinate, cellulose acetate maleate, cellulose benzoate phthalate, cellulose propionate phthalate, methylcellulose phthalate, carboxymethylethylcellulose, ethylhydroxyethylcellulose phthalate, and methylhydroxyethylcellulose; enteric acrylic acid cellulose such as a styrene/acrylic acid cellulose, a methyl acrylate/acrylic acid cellulose, a methyl acrylate/methacrylic acid cellulose (e.g., Acryl-EZE), a butyl acrylate/styrene/acrylic acid cellulose r, and a methyl acrylate/methacrylic acid/octyl acrylate cellulose; enteric methacrylic acid cellulose such as a poly(methacrylic acid/methyl methacrylate) cellulose (e.g., Eudragit L or Eudragit S, Evonik, Germany), and a poly (methacrylic acid/ethyl acrylate) cellulose (e.g., Eudragit L100-55, Evonik, Germany); enteric maleic acid cellulose such as a vinyl acetate/maleic acid cellulose, a styrene/maleic cellulose, a styrene/maleic monoester cellulose, a vinyl methyl ether/maleic acid cellulose, an ethylene/maleic acid cellulose, a vinyl butyl ether/maleic acid cellulose, an acrylonitrile/methyl acrylate/maleic acid cellulose, and a butyl acrylate/styrene/maleic acid cellulose; and enteric polyvinyl derivatives such as nitril alcohol phthalate, nitrilacetal phthalate, polyvinylbutyrate phthalate, and polyvinylacetacetal phthalate.

The water-insoluble polymer refers to a pharmaceutically acceptable water-insoluble polymer which controls the release of a drug. Examples of the water-insoluble polymer include polyvinyl acetate (e.g. Kollicoat SR30D), a water-insoluble polymethacrylate copolymer {e.g. poly(ethyl acrylate-methyl methacrylate) copolymer (such as Eudragit NE30D, a poly(ethyl acrylate-methyl methacrylate-trimethylaminoethyl methacrylate) copolymer (e.g. Eudragit RSPO) }, ethylcellulose, cellulose ester, cellulose ether, cellulose acylate, cellulose diacylate, cellulose triacylate, cellulose acetate, cellulose diacetate, and cellulose triacetate.

The hydrophobic compound refers to a pharmaceutically acceptable water-insoluble material which controls the release of a drug. Examples of the hydrophobic compound include fatty acids and fatty acid esters such as glyceryl palmitostearate, glyceryl stearate, glyceryl behenate, cetyl palmitate, glyceryl monooleate and stearic acid; fatty acid alcohols such as cetostearyl alcohol, cetyl alcohol and stearyl alcohol; waxes such as carnauba wax, beeswax and microcrystalline wax; and inorganic materials such as talc, precipitated calcium carbonate, calcium hydrogen phosphate, zinc oxide, titanium oxide, kaolin, bentonite, montmorillonite and veegum.

The hydrophilic polymer refers to a pharmaceutically acceptable water-soluble polymer which controls the release of a drug. Examples of the hydrophilic polymer include saccharides such as dextrin, polydextrin, dextran, pectin and a pectin derivative, alginate, polygalacturonic acid, xylan, arabinoxylan, arabinogalactan, starch, hydroxypropyl starch, amylose and amylopectin; cellulose derivatives such as hypromellose, hydroxypropylcellulose, hydroxymethylcellulose, hydroxyethylcellulose, methylcellulose, and sodium carboxymethylcellulose; gums such as guar gum, locust bean gum, tragacanth, carrageenan, gum acacia, gum arabic, gellan gum and xanthan gum; proteins such as gelatin, casein and zein; polyvinyl derivatives such as polyvinyl alcohol, polyvinyl pyrrolidone and polyvinylacetal diethylaminoacetate; hydrophilic polymethacrylate copolymers such as a poly(butyl methacrylate-(2-dimethylaminoethyl)methacrylate-methyl methacrylate) copolymer (e.g. Eudragit E100, Evonik, Germany), and a poly(ethyl acrylate-methyl methacrylate-triethylaminoethyl-methacrylate chloride) copolymer (e.g. Eudragit RL and RS, Evonik, Germany); polyethylene derivatives such as polyethylene glycol and polyethylene oxide; and carbomer.

In addition, the composition of the present invention may optionally contain pharmaceutically acceptable additives such as various additives selected from colorants and fragrances.

The range of the additive that can be used in the present invention is not limited to the above-mentioned additives, and the additive may be used in a conventional dose which can be appropriately selected by those skilled in the art.

The pharmaceutical composition in accordance with the present invention may be formulated into an oral dosage form such as a powder, a granule, a tablet, a capsule, a suspension, an emulsion, a syrup or an aerosol, external use dosage form, suppository dosage form or a parenteral dosage form such as an agent for a sterile injection, according to a conventional known method.

Further, the present invention provides a use of a compound represented by formula I in accordance with the present invention, the above-exemplified compounds, or pharmaceutically acceptable salts thereof, for manufacturing a pharmaceutical formulation for reducing anticancer drug resistance.

Further, the present invention provides a method for reducing anticancer drug resistance, including administering, to a mammal, a compound represented by formula I, the above-exemplified compounds or pharmaceutically acceptable salts thereof. As used herein, the term "administering" means the introduction of the pharmaceutical composition of the present invention to a patient via any appropriate method. The pharmaceutical composition of the present invention may be administered via any conventional administration route as long as the pharmaceutical composition can reach a target tissue. For example, the composition may be administered orally, intraperitoneally, intravenously, intramuscularly, subcutaneously, transdermally, intranasally, intrapulmonary, rectally, intracavitally, intrathecally or subdurally without being limited thereto.

The pharmaceutical composition of the present invention may be administered once a day or may be administered at regular time intervals twice or more a day. The pharmaceutical composition of the present invention may be administered concurrently with an anticancer drug or may be administered with an anticancer drug at regular time intervals.

A dose of the compound represented by formula I in accordance with the present invention or the above-exemplified compounds is preferably in a range of 0.01 mg/kg/day to 100 mg/kg/day, and more preferably 0.1 mg/kg/day to 10 mg/kg/day, but may vary depending on age and sex of the patient, and severity of the disease. In addition, the anticancer-aiding composition of the present invention is preferably used in a dose of about 1 to 10 times that of the anticancer drug to be used, but may vary depending on sex, age and specificity of the patient, and severity of the disease.

Further, the present invention provides a method for reducing resistance of cancer cells to an anticancer drug, including contacting the cancer cells with the compound represented by formula I or a pharmaceutically acceptable salt thereof.

The compound represented by formula I or a pharmaceutically acceptable salt thereof inhibits the activity of the P-glycoprotein in cancer cells. Accordingly, cellular efflux of an anticancer drug administered to the cancer cells is prevented such that intracellular accumulation of the anticancer drug can be achieved at a certain concentration to provide effective death of the cancer cells by the anticancer drug. As a result, growth or survival of cancer can be easily suppressed by an anticancer drug.

Advantageous Effects

As described above, the compounds of the present invention can inhibit the activity of the P-glycoprotein (P-gp) to prevent cellular efflux of an anticancer drug such that accumulation of the anticancer drug in cancer cells is increased to thereby suppress the growth of cancer. Therefore, the compounds of the present invention can be usefully used as an anticancer-aiding composition for the prevention or treatment of cancer diseases.

MODE FOR INVENTION

Hereinafter, the present invention will be described in more detail with reference to the following Examples and Experimental Examples. However, it should be understood that the following Examples are provided only for illustrating the present invention and should not be construed as limiting the scope and spirit of the present invention.

Unless otherwise specifically indicated, reagents used hereinafter were special-grade reagents and first-grade reagents purchased from Sigma-Aldrich, Merck, Acros, Fluka or the like. A TLC plate was a Kieselgel 60 $F_{254}$ (Art. 5715) from Merck, and silica gel for column chromatography was a Silica gel 60 (0.040-0.063 mm ASTM) from Merck.

$^1$H-NMR and $^{13}$C-NMR spectra were measured using a Varian Gemini Spectrometer 200 MHz, Bruker 250 MHz spectrometer or Varian NMR AS 400 MHz. The chemical shifts (δ) are expressed in parts per million (ppm) downfield from the tetramethylsilane (TMS) internal standard. The coupling constant (J) is expressed in Hz. The melting point was measured using Barnstead International MEL-TEMP 1202D, and temperature correction has not been made.

The hydrogen redactor was a parr hydrogenation apparatus, and mass spectra were taken using an LCQ advantage-trap mass spectrometer (Thermo Finnigan, San Jose, Calif., USA) equipped with an electrospray ionization source and a GC-2010 (Shimadzu) equipped with an electron ionization unit.

EXAMPLE 1

Synthesis of 3-(3-chloro-2-hydroxypropoxy)-1-hydroxy-5-methoxy-9H-xanthen-9-one (Compound 1)

Step 1: Synthesis of 1,3-dihydroxy-5-methoxy-9H-xanthen-9-one 2,3-dimethoxybenzoic acid (0.91 g, 5 mmol), phloroglucinol (0.95 g, 7.5 mmol), ZnCl☐ (4.69 g, 30 mmol) and POCl☐ (20 mL) were charged to a dry round-bottom flask, followed by stirring at 80° C. for 4 hours. After the reaction was completed, the reaction mixture was cooled to room temperature and was very slowly added to 500 mL of ice water. When the reaction liquid was poured in ice water, ice was added portionwise to prevent overheating. The resulting precipitate was allowed to stand at 4° C. overnight, combined, washed with water and ether, and then dried under reduced pressure to give the title compound (1.22 g, 94.8%) as a reddish brown solid.

$^1$H-NMR (250 MHz, DMSO-$d_6$) δ 3.96 (s, 3H, C5-OCH$_3$), 6.21 (d, J=2.1 Hz, 1H, C2-H), 6.40 (d, J=2.1 Hz, 1H, C4-H), 7.36 (dd, J=8.0, 7.9 Hz, 1H, C7-H), 7.49 (dd, J=1.3, 8.0 Hz, 1H, C6-H), 7.64 (dd, J=1.3, 7.9 Hz, 1H, C8-H), 11.06 (br s, 1H, C3-OH), 12.8 (s, 1H, C1-OH).

Step 2: Synthesis of 1-hydroxy-5-methoxy-3-(oxiran-2-ylmethoxy)-9H-xanthen-9-one A mixture of 1,3-dihydroxy-5-methoxy-9H-xanthen-9-one (1.13 g, 4.39 mmol) prepared in Step 1 of Example 1 and $K_2CO_3$ (1.52 g, 10.98 mmol) in anhydrous acetone (25 mL) was charged to a dry round-bottom flask, and epichlorohydrin (1.73 mL, 21.95 mmol) was added thereto, followed by stirring under reflux at a temperature of 55 to 60° C. for 6 hours. Solid of the reaction mixture was filtered, and the solvent was removed under reduced pressure. The resulting residue was separated and purified by silica gel column chromatography (developing solvent: ethyl acetate:n-hexane=1:1 (v/v)) to give the title compound (443.2 mg, 32%) as a light yellow solid.

m.p. 182° C.; Rf 0.43 (developing solvent: ethyl acetate:hexane=1:1 (v/v));

$^1$H-NMR (250 MHz, CDCl$_3$) δ 2.93 (dd, J=4.3, 4.8 Hz, 1H, C3'-Hb), 2.76 (dd, J=2.6, 4.8 Hz, 1H, C3'-Ha), 3.36-3.40 (m, 1H, C-2'H), 3.99 (dd, J=6.0, 11.0 Hz, 1H, C1'-Ha), 4.01 (s, 3H, C5-OCH3), 4.31 (dd, J=2.9, 11.0 Hz, 1H, C1'-Hb), 6.36 (d, J=2.3 Hz, 1H, C2-H), 6.56 (d, J=2.3 Hz, 1H, C4-H), 7.20-7.32 (m, 2H, C6,7-H), 7.80 (dd, J=1.7, 7.7 Hz, 1H, C8-H), 12.81 (s, 1H, C1-OH);

$^{13}$C-NMR (62.5 MHz, CDCl$_3$) 44.6 (C3'), 49.7 (C2'), 56.4 (C5-OCH3), 69.2 (C1'), 93.3 (C4), 100.0 (C2), 104.2 (C9a), 115.7 (C6), 116.7 (C8), 121.5 (C8a), 123.7 (C7), 146.3 (C10a), 148.3 (C5), 157.5 (C4a), 163.3 (C1), 165.4 (C3), 180.9 (C9) ppm;

LC-ESI: m/e 315.3 [M+1]$^+$.

Step 3: Synthesis of 3-(3-chloro-2-hydroxypropoxy)-1-hydroxy-5-methoxy-9H-xanthen-9-one (Compound 1)

Aqueous ethyl acetate 1M-HCl (3 mL) was added to 1-hydroxy-5-methoxy-3-(oxiran-2-ylmethoxy)-9H-xanthen-9-one (30 mg, 0.10 mmol) synthesized in Step 2 of Example 1, followed by stirring at room temperature for 30 minutes, and the reaction solvent was removed under reduced pressure. Ether was added to the residue, followed by sonication, and the solvent was removed to obtain the title compound (31 mg, 92%) as a light brown solid.

m.p. 184° C.;

$^1$H-NMR (400 MHz, CDCl$_3$) δ 3.60-3.73 (m, 2H, C3'-H), 3.95 (s, 3H, C$_5$—OCH$_3$), 4.09 (m, 2H, C1'-H), 4.13-4.19 (m, 1H, C-2'H), 6.30 (s, 1H, C2-H), 6.52 (s, 1H, C4-H), 7.16 –7.27 (m, 2H, C6,7-H), 7.72 (dd, J=2.0, 7.6 Hz, 1H, C8-H);

$^{13}$C-NMR (62.5 MHz, CDCl$_3$) 45.5 (C3'), 56.3 (C5-OCH3), 69.1 (C1'), 69.1 (C2'), 93.2 (C4), 97.9 (C2), 104.0 (C9a), 115.8 (C6), 116.6 (C8), 121.3 (C8a), 123.7 (C7), 146.2 (C10a), 148.1 (C5), 157.5 (C4a), 163.3 (C1), 165.4 (C3), 180.8 (C9) ppm;

LC-ESI: m/e 351.1 [M+1]+.

EXAMPLE 2

Synthesis of 3-(3-chloro-2-hydroxypropoxy)-1-hydroxy-9H-xanthen-9-one (Compound 2)

Step 1: Synthesis of 1,3-dihydroxy-9H-xanthen-9-one

Salicylic acid (1.25 g, 9.1 mmol), phloroglucinol (1.26 g, 10 mmol), ZnCl☐(3.1 g, 22.8 mmol) and POCl☐ (8 mL)

were charged to a dry round-bottom flask, and the reaction mixture was stirred at 80° C. for 4 hours. After the reaction was completed, the reaction mixture was cooled to room temperature and was very slowly added to ice water. When the reaction liquid was poured in ice water, ice was added portionwise to prevent overheating. The resulting precipitate was allowed to stand at 4° C. overnight, combined, washed with water and ether, and then dried under reduced pressure to give a reddish brown solid compound (1.94 g, 93%).

$^1$H-NMR (250 MHz, DMSO-$d_6$) δ 6.21 (d, J=2.0 Hz, 1H, C2-H), 6.40 (d, J=2.0 Hz, 1H, C4-H), 7.45 (dd, J=7.7, 8.1 Hz 1H, C7-H), 7.58 (d, J=8.1 Hz, 1H, C5-H), 7.84 (dd, J=7.7, 7.9 Hz, 1H, C6-H), 8.12 (dd, J=1.3, 7.9 Hz, 1H, C8-H), 11.08 (s, 1H, C3-OH), 12.8 (s, 1H, C1-OH).

Step 2: Synthesis of 1-hydroxy-3-(oxiran-2-yl-methoxy)-9H-xanthen-9-one 1,3-dihydroxy-9H-xanthen-9-one (1 g, 4.39 mmol) prepared in Step 1 of Example 2 and $K_2CO_3$ (1.52 g, 10.98 mmol) were added to a dry round-bottom flask, and anhydrous acetone (25 ml) was added thereto. Epichlorohydrin (1.73 mL, 21.95 mmol) was added dropwise to the reaction mixture, and the reaction liquid was stirred under reflux at a temperature of 55 to 60° C. for 6 hours. After the reaction was completed, the solvent was removed under reduced pressure. The resulting residue was separated and purified by silica gel column chromatography (developing solvent: ethyl acetate:n-hexane=1:1 (v/v)) to give the title compound (0.28 g, 22%) as a light brown solid.

m.p. 197° C.; R/0.42 (developing solvent: ethylacetate:hexane=1:1 (v/v));

$^1$H-NMR (250 MHz, CDCl$_3$) δ 2.77 (dd, J=2.6, 4.6 Hz, 1H, C3'-Ha), 2.93 (dd, J=4.3, 4.6 Hz, 1H, C3'-Hb), 3.36-3.39 (m, 1H, C-2'H), 3.99 (dd, J=5.9, 11.1 Hz, 1H, C1'-Ha), 4.33 (dd, J=2.8, 11.1 Hz, 1H, C1'-Hb), 6.34 (d, J=2.2 Hz, 1H, C2-H), 6.44 (d, J=2.2 Hz, 1H, C4-H), 7.3-7.42 (m, 2H, C5,7-H), 7.70 (ddd, J=1.4, 7.8, 7.8 Hz, 1H, C6-H), 8.22 (dd, J=1.4, 7.9 Hz, 1H, C8-H), 12.85 (s, 1H, C1-OH);

$^{13}$C-NMR (62.5 MHz, CDCl$_3$) 44.6 (C3'), 49.7 (C2'), 69.2 (C1'), 93.4 (C4), 97.4 (C2), 104.2 (C9a), 117.6 (C5), 120.6 (C8a), 124.1 (C7), 125.9 (C8), 135.1 (C6), 156.0 (C10a), 157.6 (C4a), 163.3 (C1), 165.4 (C3), 180.9 (C9) ppm; LC-ESI: m/e 285.2 [M+1]+.

Step 3: Synthesis of 3-(3-chloro-2-hydroxypropoxy)-1-hydroxy-9H-xanthen-9-one An aqueous ethyl acetate 1M-HCl (3 mL) was added to 1-hydroxy-3-(oxiran-2-ylmethoxy)-9H-xanthen-9-one (30 mg, 0.11 mmol) prepared in Step 2 of Example 2, followed by stirring at room temperature for 30 minutes, and the reaction solvent was removed under reduced pressure. Ether was added to the residue, followed by sonication, and the solvent was removed to give the title compound (32 mg, 94.1%) as a red solid.

m.p. 144° C.;

$^1$H-NMR (250 MHz, CDCl$_3$) δ 3.70-3.83 (m, 2H, C3'-H), 4.16 (m, 2H, C1'-H), 4.24-4.26 (m, 1H, C-2'H), 6.34 (d, J=1.9 Hz, 1H, C2-H), 6.44 (d, J=1.9 Hz, 1H, C4-H), 7.34-7.43 (m, 2H, C5,7-H), 7.71 (dd, J=7.9, 8.2 Hz, 1H, C6-H), 8.23 (d, J=7.9 Hz, 1H, C8-H), 12.85 (s, 1H, C1-OH);

$^{13}$C-NMR (62.5 MHz, CDCl$_3$) 46.0 (C3'), 69.1 (C1'), 69.6 (C2'), 93.4 (C4), 97.6 (C2), 104.4 (C9a), 117.7 (C5), 120.7 (C8a), 124.2 (C7), 126.0 (C8), 135.2 (C6), 156.1 (C10a), 157.8 (C4a), 163.3 (C1), 165.2 (C3), 180.9 (C9) ppm;

LC-ESI: m/e 321.2 [M+1]+.

EXAMPLE 3

Synthesis of 1-hydroxy-5-methoxy-3-(thiiran-2-yl-methoxy)-9H-xanthen-9-one (Compound 3)

A mixture of 1,3-dihydroxy-5-methoxy-9H-xanthen-9-one (513 mg, 1.99 mmol) prepared in Step 1 of Example 1 and $K_2CO_3$ (548 mg, 3.96 mmol) in anhydrous acetone (15 mL) was charged to a dry round-bottom flask, and epichlorohydrin (1.08 g, 9.93 mmol) was added thereto, followed by stirring with reflux at a temperature of 55 to 60° C. for 6 hours. Solid of the reaction mixture was filtered, and the solvent was removed under reduced pressure. The resulting residue was separated and purified by silica gel column chromatography (developing solvent: ethyl acetate:n-hexane=1:1 (v/v)) to give the title compound (104 mg, 15.9%) as a yellow solid.

m.p. 187° C.; Rf 0.69 (ethyl acetate:n-hexane=1:1 (v/v));

$^1$H-NMR (200 MHz, CDCl$_3$) δ 2.37 (dd, J=0.8, 5.2 Hz, 1H, C3'-Ha), 2.66 (d, J=5.2 Hz, 1H, C3'-Hb), 3.30-3.34 (m, 1H, C-2'H), 4.01 (dd, J=6.9, 10.4 Hz, 1H, C1'-Ha), 4.04 (s, 3H, C5-OCH3), 4.28 (dd, J=5.6, 10.4 Hz, 1H, C1'-Hb), 6.37 (d, J=2.2 Hz, 1H, C2-H), 6.55 (d, J=2.2 Hz, 1H, C4-H), 7.24-7.32 (m, 2H, C6,7-H), 7.82 (dd, J=1.8, 7.6 Hz, 1H, C8-H), 12.83 (s, 1H, C1-OH);

$^{13}$C-NMR (50 MHz, CDCl$_3$) 24.0 (C3'), 30.9 (C2'), 56.6 (C5-OCH3), 73.1 (C1'), 93.2 (C4), 98.1 (C2), 104.3 (C9a), 115.8 (C6), 116.8 (C8), 121.6 (C8a), 123.8 (C7), 146.3 (C10a), 148.3 (C5), 157.6 (C4a), 163.3 (C1), 165.3 (C3), 180.8 (C9) ppm;

LC-ESI: m/e 331.1 [M+1]+.

EXAMPLE 4

Synthesis of 1,3-bis(thiiran-2-ylmethoxy)-9H-xanthen-9-one (Compound 4)

Epithiochlorohydrin (0.86 g, 7.94 mmol) was added dropwise to a mixture of 1,3-dihydroxy-9H-xanthen-9-one (0.18 g, 0.79 mmol) synthesized in Step 1 of Example 2 and $Cs_2CO_3$ (1.55 g, 4.76 mmol) in anhydrous acetone (10 mL), followed by stirring under reflux at a temperature of 55 to 60° C. for 6 hours. After the reaction was completed, the solid was removed by filtration, and the solvent of the filtrate was distilled off under reduced pressure. The resulting residue was separated and purified by silica gel column chromatography (developing solvent: ethyl acetate:n-hexane=1:1 (v/v)) to give the title compound (46 mg, 15.6%) as a brown gel.

Rf 0.68 (ethyl acetate:n-hexane=1:1 (v/v));

$^1$H-NMR (400 MHz, CDCl$_3$) δ 2.30 (dd, J=1.6, 5.2 Hz, 1H, C3'-Ha), 2.45 (d, J=5.6 Hz, 1H, C3"-Ha), 2.59 (d, J=6.4 Hz, 1H, C3'-Hb), 2.64 (d, J=5.6 Hz, 1H, C3"-Hb), 3.19-3.26 (m, 1H, C-2'H), 3.38-3.45 (m, 1H, C2"-H), 3.88 (dd, J=7.4, 10.2 Hz, 1H, C1"-Ha), 3.98 (dd, J=7.0, 10.0 Hz, 1H, C1'-Ha), 4.19 (dd, J=5.8, 10.0 Hz, 1H, C1'-Hb), 4.39 (dd, J=4.6, 10.2 Hz, 1H, C1"-Hb), 6.30 (d, J=2.4 Hz, 1H, C2-H), 6.44 (d, J=2.4 Hz, 1H, C4-H), 7.25-7.31 (m, 2H, C5,7-H), 7.57 (ddd, J=1.7, 7.2, 8.4 Hz, 1H, C6-H), 8.22 (dd, J=1.7, 7.8 Hz, 1H, C8-H);

$^{13}$C-NMR (100 MHz, CDCl$_3$) 23.9 (C3'), 24.7 (C3"), 30.9 (C2'), 31.2 (C2"), 73.1 (C1'), 73.9 (73.8) (C1"), 94.4 (C4), 97.4 (C2), 108.1 (C9a), 117.2 (C5), 123.2 (C8a), 124.2 (C7), 126.9 (C8), 134.1 (C6), 155.2 (C10a), 159.9 (C4a), 163.3 (C1), 163.6 (C3), 175.5 (C9) ppm; LC-ESI: m/e 373.0 [M+1]$^+$, 395.0 [M+Na]$^+$.

EXAMPLE 5

Synthesis of 1,3-bis(thiiran-2-ylmethoxy)-5-methoxy-9H-xanthen-9-one (Compound 5)

Epithiochlorohydrin (1.08 g, 9.91 mmol) was added dropwise to a mixture of 1,3-dihydroxy-5-methoxy-9H-xanthen-9-one (256 mg, 0.99 mmol) prepared in Step 1 of Example 1 and $Cs_2CO_3$ (1.94 g, 5.96 mmol) in anhydrous acetone (10 mL), followed by stirring under reflux at a temperature of 55 to 60° C. for 6 hours. After the reaction was completed, the solid was removed by filtration, and the solvent of the filtrate was distilled off under reduced pressure. The resulting residue was purified by silica gel column chromatography (developing solvent: ethyl acetate:n-hexane=1:1 (v/v)) to give the title compound (31 mg, 7.5%) as a light brown solid.

m.p. 240° C.>;
$R_f$ 0.65 (ethyl acetate:n-hexane=1:1 (v/v));
$^1$H-NMR (400 MHz, $CDCl_3$) δ 2.28 (dd, J=1.2, 5.2 Hz, 1H), 2.45 (d, J=5.6 Hz, 1H, C3"-Ha), 2.57 (d, J=6.0 Hz, 1H, C3'-Hb), 2.64 (d, J=5.6 Hz, 1H, C3"-Hb), 3.20-3.25 (m, 1H, C-2'H, C3'-Ha), 3.37-3.43 (m, 1H, C2"-H), 3.87 (dd, J=7.4, 10.2 Hz, 1H, C1"-Ha), 3.94 (s, 3H, C5-OCH3), 3.97 (dd, J=3.6, 10.2, Hz, 1H, C1'-Ha), 4.17 (dd, J=6.0, 10.2 Hz, 1H, C1'-Hb), 4.38 (dd, J=4.6, 10.2 Hz, 1H, C1"-Hb), 6.31 (d, J=2.4 Hz, 1H, C2-H), 6.56 (d, J=2.4 Hz, 1H, C4-H), 7.10 (dd, J=1.2, 8.0 Hz, 1H, C6-H), 7.18 (dd, J=8.0, 8.0 Hz, 1H, C7-H), 7.79 (dd, J=1.2, 8.0 Hz, 1H, C8-H);
$^{13}$C-NMR (100 MHz, $CDCl_3$) 23.9 (C3'), 24.7 (C3"), 30.9 (C2'), 31.1 (C2"), 56.6 (C5-OCH3), 73.2 (C1'), 73.9 (C1"), 94.4 (C4), 97.7 (C2), 108.0 (C9a), 114.8 (C6), 117.9 (C8), 123.6 (C7), 124.2 (C8a), 145.5 (C10a), 148.2 (C5), 159.7 (C4a), 163.3 (C1), 163.6 (C3), 175.4 (C9) ppm;
LC ESI: m/e 403.0 $[M+1]^+$, 425.1 $[M+Na]^+$.

EXAMPLE 6

Synthesis of 3-(2,3-dihydroxypropoxy)-1-hydroxy-9H-xanthen-9-one (Compound 6)

1-hydroxy-3-(oxiran-2-ylmethoxy)-9H-xanthen-9-one (30 mg, 0.11 mmol) synthesized in Step 2 of Example 2 and 50% trifluoroacetic acid (TFA) (5 mL) were charged to a round-bottom flask, followed by stirring at 50° C. for 4 hours. After the reaction was completed, the solvent was removed, followed by drying under reduced pressure to give the title compound (20 mg, 62.7%) as a light yellow solid.

m.p. 170° C.;
$R_f$ 0.12 (ethyl acetate:n-hexane=1:1 (v/v));
$^1$H-NMR (400 MHz, DMSO-d6) δ 3.39 (dd, J=5.4, 5.4 Hz, 2H, C3'-H), 3.75-3.37 (m, 1H, C-2'H), 3.97 (dd, J=6.4, 10.4 Hz, 1H, C1'-Ha), 4.11 (dd, J=3.6, 10.4 Hz, 1H, C1'-Hb), 4.70 (t, J=5.6 Hz, 1H, C3'-OH), 5.01 (d, J=5.2 Hz, 1H, C2'-OH), 6.35 (d, J=2.0 Hz, 1H, C2-H), 6.59 (d, J=2.0 Hz, 1H, C4-H), 7.44 (dd, J=7.0, 7.6 Hz, 1H, C7-H), 7.56 (d, J=8.4 Hz, 1H, C5-H), 7.82 (ddd, J=1.6, 7.0, 8.4 Hz, 1H, C6-H), 8.07 (dd, J=1.6, 7.6 Hz, 1H, C8-H), 12.73 (s, 1H, C1-OH);
$^{13}$C-NMR (100 MHz, DMSO-d6) 63.2 (C3'), 70.5 (C1'), 71.4 (C2'), 94.0 (C4), 98.3 (C2), 103.8 (C9a), 118.5 (C5), 120.6 (C8a), 125.3 (C7), 126.0 (C8), 136.6 (C6), 156.2 (C10a), 158.0 (C4a), 163.3 (C1), 166.9 (C3), 180.8 (C9) ppm;
LC-ESI: m/e 303.2 $[M+1]^+$.

EXAMPLE 7

Synthesis of 3-(2,3-dihydroxypropoxy)-1-hydroxy-5-methoxy-9H-xanthen-9-one (Compound 7)

50% TFA (5 mL) was added to 1-hydroxy-5-methoxy-3-(oxiran-2-ylmethoxy)-9H-xanthen-9-one (20 mg, 0.06 mmol) synthesized in Step 2 of Example 1, and the reaction mixture was stirred at 50° C. for 4 hours. The solvent was removed, and the resulting residue was dried under reduced pressure to give the title compound (10 mg, 47.3%) as a white solid.

m.p. 189° C.; $R_f$ 0.14 (ethyl acetate:n-hexane=1:1 (v/v));
$^1$H-NMR (400 MHz, acetone-d6) δ 3.41 (dd, J=5.6, 5.6 Hz, 2H, C3'-H), 3.76-3.80 (m, 1H, C-2'H), 3.95 (s, 3H, C5-OCH3), 4.00 (dd, J=5.2, 10.1 Hz, 1H, C1'-Ha), 4.14 (dd, J=3.6, 10.1 Hz, 1H, C1'-Hb), 4.71 (t, J=5.6 Hz, 1H, C3'-OH), 5.04 (d, J=5.2 Hz, 1H, C2'-OH), 6.37 (d, J=2.0 Hz, 1H, C2-H), 6.65 (d, J=2.0 Hz, 1H, C4-H), 7.38 (dd, J=7.8, 8.0 Hz, 1H, C7-H), 7.50 (dd, J=1.5, 8.0 Hz, 1H, C6-H), 7.65 (dd, J=1.5, 7.8 Hz, 1H, C8-H), 12.74 (s, 1H, C1-OH);
$^{13}$C-NMR (100 MHz, acetone-d6) 63.2 (C3'), 56.1 (C5-OCH3), 70.4 (C1'), 70.6 (C2'), 93.2 (C4), 98.0 (C2), 103.7 (C9a), 116.1 (C6), 116.6 (C8), 124.2 (C7), 124.2 (C8a), 146.7 (10a), 148.8 (C5), 157.9 (C4a), 163.5 (C1), 165.8 (C3), 180.9 (C9) ppm;
LC-ESI: m/e 333.2 $[M+1]^+$.

EXAMPLE 8

Synthesis of 1-hydroxy-3-(thiiran-2-ylmethoxy)-9H-thioxanthen-9-one (Compound 8)

Step 1: Synthesis of 1,3-dihydroxy-9H-thioxanthen-9-one

A mixture of phosphorous pentoxide (3.71 g, 26.15 mmol) and methane sulfonic acid (27.05 mL, 0.42 mmol) was stirred at 90° C. for about one hour until a clear solution was obtained. To the reaction solution were added thiosalicylic acid (1.04 g, 6.76 mmol) and phloroglucinol (1.02 g, 8.11 mmol), followed by stirring at 70° C. for 10 minutes. After the reaction was completed, the reaction mixture was poured in 1 L of ice water. The resulting precipitate was allowed to stand at 4° C. overnight, combined, washed with water, and then dried under reduced pressure to give an orange solid compound. This compound was separated and purified by silica gel column chromatography (developing solvent: ethyl acetate:n-hexane=1:1 (v/v)) to give a yellow solid compound (1.14 g, 51.1%).

$^1$H-NMR (200 MHz, acetone-$d_6$) δ 6.38 (d, J=2.2 Hz, 1H, C4-H), 6.64 (d, J=2.2 Hz, 1H, C2-H), 7.55 (ddd, J=1.8, 6.8, 8.2 Hz, 1H, C7-H), 7.64-7.79 (m, 2H, C5-H, C6-H), 8.50 (dd, J=1.2, 8.0 Hz, 1H, C8-H), 14.42 (s, 1H, C1-OH).

Step 2: Synthesis of 1-hydroxy-3-(thiiran-2-ylmethoxy)-9H-thioxanthen-9-one (Compound 8)

Epithiochlorohydrin (0.22 g, 2.05 mmol) was added dropwise to a mixture of 1,3-dihydroxy-9H-thioxanthen-9-one (100 mg, 0.41 mmol) prepared in Step 1 of Example 8 and $K_2CO_3$ (113 mg, 0.82 mmol) in anhydrous acetone (15 mL) in a dry round-bottom flask, followed by stirring under reflux for one day at a temperature of 55 to 60° C.

Solid of the reaction mixture was filtered, and the solvent was removed under reduced pressure. The resulting residue was separated and purified by silica gel column chromatography (developing solvent: ethyl acetate:n-hexane=1:1 (v/v)) to give the title compound (43 mg, 33.2%) as a light green solid.

m.p. 149° C.; $R_f$ 0.89 (ethyl acetate:n-hexane=1:1 (v/v));
$^1$H-NMR (400 MHz, $CDCl_3$) δ 2.27 (dd, J=1.4, 5.7 Hz, 1H, C3'-Ha), 2.56 (d, J=5.7 Hz, 1H, C3'-Hb), 3.16-3.21 (m, 1H, C-2'H), 3.92 (dd, J=7.2, 10.0 Hz, 1H, C1'-Ha), 4.13 (dd, J=5.6, 10.0 Hz, 1H, C1'-Hb), 6.12 (d, J=2.4 Hz, 1H, C4-H), 6.50 (d, J=2.4 Hz, 1H, C2-H), 7.36 (ddd, J=1.4, 6.8, 7.8 Hz, 1H, C7-H), 7.37 (d, J=8.2 Hz, 1H, C5-H), 7.49 (ddd, J=1.6, 8.0, 8.2 Hz, 1H, C6-H), 8.43 (dd, J=1.4, 7.8 Hz, 1H, C8-H);
$^{13}$C-NMR (100 MHz, CDCl$_3$) 24.0 (C3'), 31.0 (CT), 72.9 (C1'), 100.2 (C4), 102.2 (C2), 109.8 (C9a), 125:6 (C5), 126.5 (C7), 128.4 (C8a), 129.4 (C8), 132.8 (C6), 137.3 (C10a), 140.6 (C4a), 163.4 (C1), 167.5 (C3), 184.3 (C9) ppm;
LC-ESI: m/e 317.1 [M+1]$^+$.

EXAMPLE 9

Synthesis of 3-(3-chloro-2-hydroxypropoxy)-1-methoxy-9H-xanthen-9-one (Compound 9)

Step 1: Synthesis of 3-benzyloxy-1-hydroxy-9H-xanthen-9-one

The compound (1.77 g, 7.75 mmol) synthesized in Step 1 of Example 2 and K$_2$CO$_3$ (2.76 g, 0.02 mol) were charged to a dry round-bottom flask, and anhydrous acetone (200 mL) was added thereto. To the reaction mixture was added benzyl bromide (1.38 mL, 11.63 mmol), followed by stirring under reflux at 60° C. for one day. After the reaction was completed, the reaction liquid was cooled to room temperature, and 200 mL of water was added thereto. The reaction liquid was acidified with 3M-HCl and extracted twice with ethyl acetate. The organic layer was combined, successively washed with water and brine, and then dried over anhydrous Na$_2$SO$_4$. The solvent was removed under reduced pressure. The resulting residue was separated and purified by silica gel column chromatography (developing solvent: CH$_2$Cl$_2$) to give the title compound (1.05 g, 42.6%) as a light yellow solid.
$^1$H-NMR (250 MHz, CDCl$_3$) δ 5.14 (s, 2H, CH$_2$ of benzyl group), 6.42 (d, J=2.3 Hz, 1H, C2-H), 6.49 (d, J=2.3 Hz, 1H, C4-H), 7.24-7.44 (m, 7H, C5-H, C7-H, proton of benzyl group), 7.70 (ddd, J=1.6, 7.2, 8.3 Hz, 1H, C6-H), 8.23 (dd, J=1.6, 7.9 Hz, 1H, C8-H), 12.85 (s, 1H, C1-OH).

Step 2: Synthesis of 3-benzyloxy-1-methoxy-9H-xanthen-9-one

The compound (0.40 g, 1.26 mmol) prepared in Step 1 of Example 9, methyl iodide (535.68 mg, 3.77 mmol), and DMF (10 mL) were charged to a dry round-bottom flask, and Cs$_2$CO$_3$ (0.82 g, 2.52 mmol) was added thereto with stirring. The reaction mixture was stirred at 50° C. for 3 hours. After the reaction was completed, the reaction liquid was transferred to an Erlenmeyer flask, and the reaction container was washed with methylene chloride. The reaction contents were combined and acidified with 2M-HCl on ice water. After being warmed to room temperature, CH$_2$Cl$_2$ (20 mL) and water (10 mL) were added and the reaction liquid was repeatedly extracted with methylene chloride. The organic layer was combined, washed with water and brine, and then dried over anhydrous Na$_2$SO$_4$. The solvent was removed under reduced pressure. Ethanol was added to the resulting sludge-like material, followed by trituration, and the resulting solid was filtered to give a white solid compound (0.41 g, 97.3%).
$^1$H-NMR (250 MHz, CDCl$_3$) δ 3.95 (s, 3H, C1-OCH$_3$), 5.15 (s, 2H, CH$_2$ of benzyl group), 6.42 (d, J=2.2 Hz, 1H, C2-H), 6.56 (d, J=2.2 Hz, 1H, C4-H), 7.24-7.47 (m, 7H, C5-H, C7-H, proton of benzyl group), 7.61 (ddd, J=1.4, 6.9, 7.0 Hz, 1H, C6-H), 8.27 (dd, J=1.4, 7.9 Hz, 1H, C8-H).

Step 3: Synthesis of 3-hydroxy-1-methoxy-9H-xanthen-9-one

The compound (120 mg) prepared in Step 2 of Example 9, Pd/C (60 mg), and anhydrous ethanol (30 mL) were added and a hydrogen gas was supplied at a pressure of 50 psi, followed by hydrogen reduction reaction for 12 hours. The reaction mixture was filtered through celite and washed with 20 mL of DMF. The filtrate was combined, and the solvent was removed under reduced pressure. The resulting residue was directly used in the next reaction without further purification.

Step 4: Synthesis of 1-methoxy-3-(oxiran-2-ylmethoxy)-9H-xanthen-9-one

The compound (87 mg, 0.36 mmol) prepared in Step 3 of Example 9 and K$_2$CO$_3$ (99.8 mg, 0.72 mmol) were charged to a dry round-bottom flask, and DMF (20 mL) was added thereto.
Epichlorohydrin (0.11 mL, 1.44 mmol) was added dropwise to the reaction mixture, followed by stirring at 70° C. for 15 hours. Water (20 mL) was added to the reaction mixture which was then extracted twice with ethyl acetate. The organic layer was combined, washed with saturated NaCl, and dried over anhydrous Na$_2$SO$_4$. The solvent was distilled off under reduced pressure. The resulting residue was purified by silica gel column chromatography (developing solvent: ethyl acetate:hexane=3:1 (v/v)) to give an orange solid compound (28 mg, 26%).
m.p. 122° C.;
Rf 0.09 (developing solvent: ethyl acetate:hexane=1:1 (v/v));
$^1$H-NMR (400 MHz, CDCl$_3$) δ 2.81 (dd, J=2.6, 4.8 Hz, 1H, C3'-Ha), 2.97 (dd, J=4.6, 4.8 Hz, 1H, C3'-Hb), 3.39-3.42 (m, 1H, C-2'H), 3.98 (s, 3H, C1-OCH3), 4.02 (dd, J=5.6, 11.4 Hz, 1H, C1'-Ha), 4.38 (dd, J=3.0, 11.4 Hz, 1H, C1'-Hb), 6.40 (d, J=2.2 Hz, 1H, C2-H), 6.50 (d, J=2.2 Hz, 1H, C4-H), 7.31-7.37 (m, 2H, C5,7-H), 7.63 (ddd, J=1.6, 7.2, 8.4 Hz, 1H, C6-H), 8.28 (dd, J=1.6, 7.6 Hz, 1H, C8-H);
$^{13}$C-NMR (100 MHz, CDCl$_3$) 44.8 (C3'), 50.0 (C2'), 56.6 (1-OCH3), 69.4 (C1'), 93.7 (C4), 95.7 (C2), 107.8 (C9a), 117.1 (C5), 123.3 (C8a), 124.1 (C7), 127.0 (C8), 134.0 (C6), 155.1 (C10a), 159.9 (C4a), 162.3 (C1), 163.8 (C3), 175.7 (C9) ppm;
LC-ESI: m/e 299.1 [M+1]$^+$.

Step 5: Synthesis of 3-(3-chloro-2-hydroxypropoxy)-1-methoxy-9H-xanthen-9-one Aqueous ethyl acetate 1M-HCl (3 mL) was added to 1-methoxy-3-(oxiran-2-ylmethoxy)-9H-xanthen-9-one (25 mg, 0.08 mmol) prepared in Step 4 of Example 9, followed by stirring at room temperature for 30 minutes, and the reaction solvent was removed under reduced pressure. Ether was added to the residue, followed by sonication, and the solvent was removed to give the title compound (20 mg, 71.3%) as a reddish brown solid.
m.p. 107° C.;
$^1$H-NMR (400 MHz, CDCl$_3$) δ 3.76-3.85 (m, 2H, C3'-H), 3.99 (s, 3H, C1-OCH$_3$), 4.20-4.22 (m, 2H, C1'-H), 4.26-4.34 (m, 1H, C-2'H), 6.38 (d, J=2.4 Hz, 1H, C2-H), 6.53 (d, J=2.4 Hz, 1H, C4-H), 7.30-7.35 (m, 2H, C5,7-H), 7.63 (ddd, J=1.6, 7.2, 8.3 Hz, 1H, C6-H), 8.29 (dd, J=1.6, 8.0 Hz, 1H, C8-H);
$^{13}$C-NMR (100 MHz, CDCl$_3$) 46.1 (C3'), 56.6 (1-OCH$_3$), 69.1 (C1'), 69.8 (C2'), 93.7 (C4), 95.5 (C2), 108.0 (C9a), 117.2 (C5), 123.3 (C8a), 124.1 (C7), 127.0 (C8), 134.0 (C6), 155.2 (C10a), 159.9 (C4a), 162.4 (C1), 163.6 (C3), 175.6 (C9) ppm;
LC-ESI: m/e 335.2 [M+1]$^+$.

EXAMPLE 10

Synthesis of 3-(3-chloro-2-hydroxypropoxy)-1-hydroxy-9H-thioxanthen-9-one (Compound 10)

Step 1: Synthesis of 1-hydroxy-3-(oxiran-2-ylmethoxy)-9H-thioxanthen-9-one

Epichlorohydrin (0.24 mL, 3.05 mmol) was added dropwise to a mixture of 1,3-dihydroxy-9H-thioxanthen-9-one (137 mg, 0.61 mmol) and $K_2CO_3$ (169 mg, 1.22 mmol) in anhydrous acetone (15 mL) in a dry round-bottom flask, followed by stirring under reflux at a temperature of 55 to 60° C. for one day. Solid of the reaction mixture was filtered and the solvent was removed under reduced pressure. The resulting residue was purified by silica gel column chromatography (developing solvent: $CH_2Cl_2$) to give the title compound (34 mg, 18.6%) as a yellow solid.

m.p. 161° C.;
$R_f$ 0.71 (developing solvent: $CH_2Cl_2$);
$^1$H-NMR (400 MHz, $CDCl_3$) δ 2.71 (dd, J=2.6, 4.6 Hz, 1H, C3'-Ha), 2.87 (dd, J=3.6, 4.6 Hz, 1H, C3'-Hb), 3.30-3.32 (m, 1H, C-2'H), 3.93 (dd, J=5.6, 11.2 Hz, 1H, C1'-Ha), 4.26 (dd, J=2.8, 11.2 Hz, 1H, C1'-Hb), 6.38 (d, J=2.6 Hz, 1H, C4-H), 6.53 (d, J=2.6 Hz, 1H, C2-H), 7.37-7.43 (m, 2H, C5,7-H), 7.53 (ddd, J=1.4, 7.6, 11.3 Hz, 1H, C6-H), 8.47 (dd, J=1.4, 8.2 Hz, 1H, C8-H);
$^{13}$C-NMR (100 MHz, $CDCl_3$) 43.6 (C3'), 48.7 (CT), 68.0 (C1'), 99.0 (C4), 101.2 (C2), 108.6 (C9a), 124.5 (C5), 127.2 (C8a), 128.2 (C7), 131.6 (C6), 131.6 (C8), 136.1 (C10a), 139.4 (C4a), 162.4 (C1), 166.4 (C3), 183.2 (C9) ppm;
LC-ESI: m/e 301.1 $[M+1]^+$.

Step 2: Synthesis of 3-(3-chloro-2-hydroxypropoxy)-1-hydroxy-9H-thioxanthen-9-one Aqueous ethyl acetate 1M-HCl (3 mL) was added to the compound (13 mg, 0.04 mmol) prepared in Step 1 of Example 10, followed by stirring at room temperature for 30 minutes, and the reaction solvent was removed under reduced pressure. Ether was added to the residue, followed by sonication, and the solvent was removed to give the title compound (14 mg, 96.0%) as a yellow solid.

m.p. 151° C.;
$^1$H-NMR (400 MHz, $CDCl_3$) δ 3.68-3.75 (m, 2H, C3'-H), 4.11 (m, 2H, C1'-H), 4.18-4.22 (m, 1H, C-2'H), 6.39 (d, J=2.4 Hz, 1H, C4-H), 6.53 (d, J=2.4 Hz, 1H, C2-H), 7.39-7.45 (m, 2H, C5,7-H), 7.54 (ddd, J=1.2, 7.5, 7.5 Hz, 1H, C6-H), 8.49 (dd, J=1.2, 8.4 Hz, 1H, C8-H);
$^{13}$C-NMR (100 MHz, $CDCl_3$) 46.0 (C3'), 69.0 (C1'), 69.7 (C2'), 100.3 (C4), 102.2 (C2), 110.0 (C9a), 125.6 (C5), 126.6 (C7), 128.4 (C8a), 129.5 (C8), 132.9 (C6), 137.3 (C10a), 140.8 (C4a), 163.3 (C1), 167.6 (C3), 184.4 (C9) ppm;
LC-ESI: m/e 337.3 $[M+1]^+$.

EXAMPLE 11

Synthesis of 3-(3-chloro-2-mercaptopropoxy)-1-hydroxy-9H-thioxanthen-9-one (Compound 11)

Aqueous ethyl acetate 1M-HCl (3 mL) was added to 1-hydroxy-3-(thiiran-2-ylmethoxy)-9H-thioxanthen-9-one (10 mg, 0.03 mmol) prepared in Example 8, followed by stirring at room temperature for 3 hours, and the reaction solvent was removed under reduced pressure. Ether was added to the residue, followed by sonication, and the solvent was removed to give the title compound (8 mg, 71.8%) as a yellow solid.

m.p. 134° C.;
$^1$H-NMR (400 MHz, $CDCl_3$) δ 2.12 (d, J=10.0 Hz, 1H, C2'-SH), 3.37-3.42 (m, 1H, C-2'H), 3.84 (dd, J=6.8, 11.3 Hz, 1H, C3'-$H_a$), 3.97 (dd, J=4.2, 11.3 Hz, 1H, C3'-$H_b$), 4.20 (dd, J=6.0, 9.6 Hz, 1H, C1'-$H_a$), 4.35 (dd, J=4.4, 9.6 Hz, 1H, C1'-$H_b$), 6.45 (d, J=2.2 Hz, 1H, C4-H), 6.59 (d, J=2.2 Hz, 1H, C2-H), 7.26-7.51 (m, 2H, C5,7-H), 7.61 (ddd, J=1.2, 7.4, 7.5 Hz, 1H, C6-H), 8.55 (d, J=7.6 Hz, 1H, C8-H);
$^{13}$C-NMR (100 MHz, $CDCl_3$) 40.0 (C2'), 46.9 (C3'), 69.0 (C1'), 100.3 (C4), 102.3 (C2), 110.0 (C9a), 125.6 (C5), 126.6 (C7), 128.4 (C8a), 129.4 (C8), 132.9 (C6), 137.3 (C10a), 140.7 (C4a), 163.2 (C1), 167.6 (C3), 184.4 (C9) ppm;
LC-ESI: m/e 353.1 $[M+1]^+$.

EXAMPLE 12

Synthesis of 8,10-bis(thiiran-2-ylmethoxy)-7H-benzo[c]xanthen-7-one (Compound 12)

Step 1: Synthesis of 8,10-dihydroxy-7H-benzo[c]xanthen-7-one

A mixture of phosphorous pentoxide (2.84 g, 0.02 mol) and methane sulfonic acid (40 mL) was stirred at 90° C. for about one hour until a clear solution was obtained. To the reaction solution were added 1-hydroxy-2-naphthoic acid (3.76 g, 0.02 mol) and phloroglucinol (3.02 g, 0.02 mmol), followed by stirring at 70° C. for 30 minutes. After the reaction was completed, the reaction mixture was poured in 1 L of ice water. The resulting solid was allowed to stand (1 d), filtered, combined, washed with water, and then dried under reduced pressure to give a red compound. This compound was separated and purified by silica gel column chromatography (developing solvent: ethyl acetate:n-hexane=1:3 (v/v)) to give a yellow solid compound (535 mg, 9.61%).

$R_f$: 0.43 (ethyl acetate:n-hexane=1:3 (v/v));
$^1$H-NMR (400 MHz, DMSO-$d_6$) δ 6.16 (s, 1H), 6.35 (s, 1H), 7.52 (dd, J=7.2, 6.8 Hz, 1H), 7.65 (dd, J=7.2, 6.8 Hz, 1H), 7.99 (s, 2H), 8.17 (d, J=8.0 Hz, 1H), 8.76 (s, 1H), 12.84 (s, 1H).

Step 2: Synthesis of 8,10-bis(thiiran-2-ylmethoxy)-7H-benzo[c]xanthen-7-one Using the compound (200 mg, 0.72 mmol) synthesized in Step 1 of Example 12, $K_2CO_3$ (198.67 mg, 1.44 mmol), DMF (20 mL), and epithiochlorohydrin (0.39 g, 3.59 mmol), silica gel column chromatography (developing solvent: ethyl acetate:n-hexane=2:1 (v/v)) was carried out to give the title compound (40 mg, 13.2%) as a white solid.

m.p. 202° C.;
$R_f$ 0.59 (ethyl acetate:n-hexane=1:1 (v/v));
$^1$H-NMR (400 MHz, $CDCl_3$) δ 2.39 (dd, J=1.4, 5.0 Hz, 1H, C3'-Ha), 2.55 (d, J=5.2 Hz, 1H, C3"-Ha), 2.68 (d, J=6.4 Hz, 1H, C3'-Hb), 2.73 (d, J=6.0 Hz, 1H, C3"-Hb), 3.30-3.35 (m, 1H, C-2'H), 3.47-3.53 (m, 1H, C2"-H), 3.97 (dd, J=7.6, 10.1 Hz, 1H, C1"-Ha), 4.09 (dd, J=6.6, 10.3 Hz, 1H, C1'-Ha), 4.31 (dd, J=5.6, 10.3 Hz, 1H, C1-Hb), 4.47 (dd, J=4.6, 10.1 Hz, 1H, C1"-Hb), 6.42 (d, J=2.4 Hz, 1H, C2-H), 6.71 (d, J=2.4 Hz, 1H, C4-H), 7.66-7.69 (m, 2H, C6,7-H), 7.72 (d, J=8.6 Hz, 1H, C9-H), 7.92 (d, J=2.0, 8.8 Hz, 1H, C8-H), 8.25 (d, J=8.6 Hz, 1H, C10-H), 8.57 (dd, J=1.6, 8.8 Hz, 1H);
$^{13}$C-NMR (100 MHz, $CDCl_3$) 23.9 (C3'), 24.7 (C3"), 30.9 (C2'), 31.1 (C2"), 73.2 (C1'), 74.0 (C1"), 94.5 (C4), 97.8 (C2), 108.7 (11a), 118.9 (C10a), 121.9 (C10), 122.7 (C5), 123.8

(C5a), 124.1 (C9), 126.9 (C6), 128.2 (C8), 129.3 (C7), 139 ((C8a), 152.3 (12a), 159.5 (C4a), 160.8 (C1), 163.2 (C3), 175.4 (C11) ppm;

LC-ESI: m/e 423.0 [M+1]$^+$445.1 [M+Na]$^+$.

EXAMPLE 13

Synthesis of 3-(3-chloro-2-mercaptopropoxy)-1-hydroxy-5-methoxy-9H-xanthen-9-one (Compound 13)

Aqueous ethyl acetate 1M-HCl (3 mL) was added to 1-hydroxy-5-methoxy-3-(thiiran-2-ylmethoxy)-9H-xanthen-9-one (30 mg, 0.09 mmol) prepared in Example 3, followed by stirring at room temperature for 3 hours, and the reaction solvent was removed under reduced pressure. Ether was added to the residue, followed by sonication, and the solvent was removed to give the title compound (30 mg, 90.1%) as a light brown solid.

m.p. 125° C.;
$^1$H-NMR (400 MHz, CDCl$_3$) δ 2.12 (d, J=10.0 Hz, 1H, C2'-SH), 3.38-3.44 (m, 1H, C-2'H), 3.84 (dd, J=6.8, 11.2 Hz, 1H, C3'-H$_a$), 3.98 (dd, J=4.4, 11.2 Hz, 1H, C3'-H$_b$), 4.03 (s, 3H, C5-OCH$_3$), 4.20 (dd, J=6.4, 9.6 Hz, 1H, C1'-H$_a$), 4.35 (dd, J=4.6, 9.4 Hz, 1H, C1'H$_b$), 6.38 (d, J=2.2 Hz, 1H, C2-H), 6.60 (d, J=2.2 Hz, 1H, C4-H), 7.25 (dd, J=1.6, 8.0 Hz, 1H, C6-H), 7.32 (dd, J=8.0, 8.0 Hz, 1H, C7-H), 7.83 (dd, J=1.6, 8.0 Hz, 1H, C8-H);
$^{13}$C-NMR (100 MHz, CDCl$_3$) 39.9 (CT), 47.0 (C3'), 56.7 (C5-OCH$_3$), 69.2 (C1'), 93.3 (C4), 98.2 (C2), 104.4 (C9a), 115.9 (C6), 116.8 (C8), 121.6 (C8a), 123.8 (C7), 146.3 (C10a), 148.3 (C5), 157.6 (C4a), 163.4 (C1), 165.1 (C3), 180.9 (C9) ppm;
LC-ESI: m/e 367.2 [M+1]$^+$.

EXAMPLES 14 AND 15

Synthesis of 11-hydroxy-9-(thiiran-2-ylmethoxy)-12H-benzo[a]xanthen-12-one (Compound 14) and 9,11-bis(thiiran-2-ylmethoxy)-12H-benzo[a]xanthen-12-one (Compound 15)

Step 1: Synthesis of 9,11-dihydroxy-12H-benzo[a]xanthen-12-one

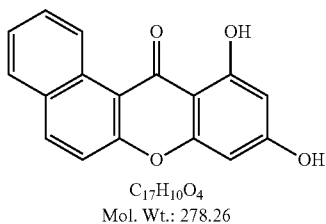 [SMILES: O=c1c2c(O)cc(O)cc2oc2ccc3ccccc3c12]

C$_{17}$H$_{10}$O$_4$
Mol. Wt.: 278.26

A mixture of 2,4,6-trihydroxybenzoic acid (1.88 g, 0.01 mol), 2-naphthol (1.44 g, 0.01 mol), ZnCl$_2$ (5.0 g, 0.036 mol) and POCl$_3$ (40 mL) was stirred under reflux at 80° C. for 5 hours. The reaction liquid was cooled to room temperature, and was very slowly added to 1 L of ice water.

When the reaction liquid was poured in ice water, ice was added portionwise to prevent overheating. The resulting solid was allowed to stand (1 d), filtered, washed with water, and then dried under reduced pressure to obtain a red compound. This compound was separated and purified by silica gel column chromatography (developing solvent: ethyl acetate:n-hexane=1:3 (v/v)) to give the title compound (202 mg, 7.23%) as a yellow solid.

Rf: 0.28 (ethyl acetate:n-hexane=1:3 (v/v));
$^1$H-NMR (400 MHz, CDCl$_3$) δ 6.26 (s, 1H), 6.38 (s, 1H), 7.42 (d, J=8.8 Hz, 1H), 7.52 (dd, J=7.6, 6.8 Hz, 1H), 7.69 (dd, J=7.2, 7.2 Hz, 1H), 7.83 (d, J=8.0 Hz, 1H), 8.04 (d, J=8.8 Hz, 1H), 9.87 (d, J=8.4 Hz, 1H).

(Compound 14)

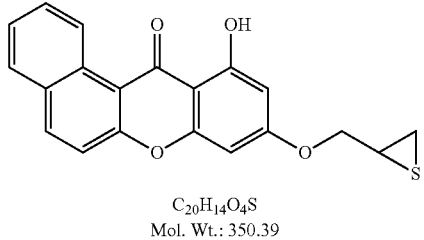

C$_{20}$H$_{14}$O$_4$S
Mol. Wt.: 350.39

(Compound 15)

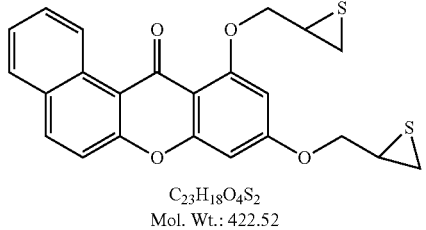

C$_{23}$H$_{18}$O$_4$S$_2$
Mol. Wt.: 422.52

Step 2: Synthesis of 11-hydroxy-9-(thiiran-2-ylmethoxy)-12H-benzo[a]xanthen-12-one (Compound 14) and 9,11-bis(thiiran-2-ylmethoxy)-12H-benzo[a]xanthen-12-one (Compound 15)

9,11-dihydroxy-12H-benzo[a]xanthen-12-one (0.1 g, 0.18 mmol) prepared in Step 1 of Examples 14 and 15, CS$_2$CO$_3$ (0.36 g, 0.54 mmol), and anhydrous acetone (13 mL) were charged to a dry round-bottom flask, and epithiochlorohydrin (0.2 g, 1.08 mmol) dissolved in anhydrous acetone (2 mL) was added thereto with stirring. The reaction mixture was stirred with reflux overnight at a temperature of 55 to 60° C. under a nitrogen atmosphere. Solid of the reaction mixture was filtered, removed and concentrated under reduced pressure. The resulting residue was separated and purified by silica gel column chromatography (developing solvent: ethyl acetate:n-hexane=1:3 (v/v)) to give a yellow solid compound 11-hydroxy-9-(thiiran-2-ylmethoxy)-12H-benzo[a]xanthen-12-one (27.3 mg, 21.7%) and a yellow solid compound 9,11-bis(thiiran-2-ylmethoxy)-12H-benzo[a]xanthen-12-one (31.2 mg, 20.5%).

11-hydroxy-9-(thiiran-2-ylmethoxy)-12H-benzo[a]xanthen-12-one: m.p: 167-168° C.; Rf: 0.66 (ethyl acetate:n-hexane=1:3 (v/v));
$^1$H-NMR (400 MHz, CDCl$_3$) δ 2.37 (d, J=5.2 Hz, 1H), 2.66 (d, J=5.2 Hz, 1H), 3.28-3.44 (m, 1H), 4.03 (dd, J=10.0, 6.8 Hz, 1H), 4.29 (dd, J=10.0, 5.6 Hz, 1H), 6.40 (d, J=2.0 Hz, 1H), 6.49 (d, J=2.0 Hz, 1H), 7.51 (d, J=9.2 Hz, 1H), 7.61 (dd, J=8.0, 7.2 Hz, 1H), 7.78 (dd, J=8.8, 7.2 Hz, 1H), 7.91 (d, J=8.0 Hz, 1H), 8.14 (d, J=8.0 Hz, 1H), 9.96 (d, J=8.8 Hz, 1H), 13.48 (s, 1H);
$^{13}$C-NMR (100 MHz, CDCl$_3$) 24.1, 31.0, 73.1, 92.7, 98.2, 105.7, 109.8, 117.8, 126.5, 127.0, 128.8, 129.8, 130.4, 131.0, 137.3, 156.7, 157.9, 163.8, 164.7, 183.2 ppm;
GC-MS (EI): m/e 350 [M]$^+$.

9,11-bis(thiiran-2-ylmethoxy)-12H-benzo[a]xanthen-12-one: m.p: 225-226° C.; Rf: 0.35 (ethyl acetate:n-hexane=1:3 (v/v));

¹H-NMR (400 MHz, CDCl₃) δ 2.38 (dd, J=5.0, 1.6 Hz, 1H), 2.55 (d, J=5.0 Hz, 1H), 2.66 (dd, J=6.0 Hz, 1H), 2.74 (d, J=6.0 Hz, 1H), 3.28-3.34 (m, 1H), 3.51-3.57 (m, 1H), 4.02 (dd, J=10.4, 7.2 Hz, 1H), 4.05 (dd, J=10.4, 7.2 Hz, 1H), 4.27 (dd, J=10.4, 5.2 Hz, 1H), 4.50 (dd, J=10.4, 4.8 Hz, 1H), 6.45 (d, J=2.0 Hz, 1H), 6.57 (d, J=2.0 Hz, 1H), 7.46 (d, J=8.8 Hz, 1H), 7.58 (dd, J=7.6, 7.2 Hz, 1H), 7.75 (dd, J=8.8, 8.0 Hz, 1H), 7.88 (d, J=8.0 Hz, 1H), 8.06 (d, J=8.8 Hz, 1H), 10.06 (d, J=8.4 Hz, 1H);

¹³C-NMR (100 MHz, CDCl₃) 24.0, 24.8, 31.0, 31.3, 73.1, 74.4, 94.0, 98.4, 110.0, 115.9, 117.5, 126.1, 127.3, 128.5, 129.4, 130.6, 131.3, 135.9, 156.3, 158.4, 160.7, 162.8, 177.5 ppm;

GC-MS (EI): m/e 422 [M]⁺.

EXAMPLES 16 AND 17

Synthesis of 11-hydroxy-9-(oxiran-2-ylmethoxy)-12H-benzo[a]xanthen-12-one (Example 16) and 9,11-bis(oxiran-2-ylmethoxy)-12H-benzo[a]xanthen-12-one (Example 17)

(Compound 16)

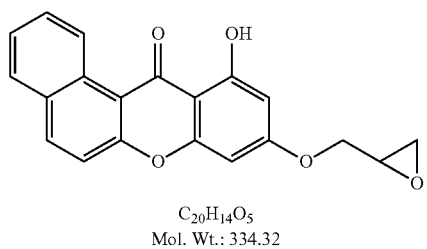

$C_{20}H_{14}O_5$
Mol. Wt.: 334.32

(Compound 17)

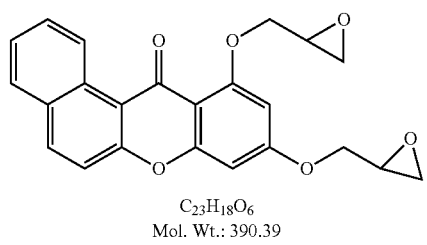

$C_{23}H_{18}O_6$
Mol. Wt.: 390.39

The compound 9,11-dihydroxy-12H-benzo[a]xanthen-12-one (0.1 g, 0.18 mmol) synthesized in Step 1 of Examples 14 and 15, CS₂CO₃ (0.36 g, 0.54 mmol), and anhydrous acetone (20 mL) were charged to a dry round-bottom flask. Under stirring, epichlorohydrin (0.2 g, 1.08 mmol) was added thereto using a syringe. The reaction liquid was stirred with reflux at a temperature of 55 to 60° C. under a nitrogen atmosphere (48 h). Solid of the reaction mixture was filtered and removed. The filtrate was concentrated under reduced pressure. The resulting residue was separated and purified by silica gel column chromatography (developing solvent: ethyl acetate:n-hexane=1:3 (v/v)) to give a yellow solid compound 11-hydroxy-9-(oxiran-2-ylmethoxy)-12H-benzo[a]xanthen-12-one (24.3 mg, 20.3%) and a yellow solid compound 9,11-bis(oxiran-2-ylmethoxy)-12H-benzo[a]xanthen-12-one (32 mg, 22.1%).

1-hydroxy-9-(oxiran-2-ylmethoxy)-12H-benzo[a]xanthen-12-one: m.p: 191-193° C.; Rf: 0.63 (ethyl acetate:n-hexane=1:1);

¹H-NMR (400 MHz, CDCl₃) δ 2.81 (dd, J=4.8, 2.4 Hz, 1H), 2.97 (dd, J=4.8, 4.4 Hz, 1H), 3.40-3.43 (m, 1H), 4.04 (dd, J=11.2, 6.0 Hz, 1H), 4.35 (dd, J=11.2, 3.2 Hz, 1H), 6.42 (d, J=2.0 Hz, 1H), 6.52 (d, J=2.0 Hz, 1H), 7.51 (d, J=8.8 Hz, 1H), 7.61 (dd, J=8.0, 3.2 Hz, 1H), 7.78 (ddd, J=8.4, 8.4, 1.6 Hz, 1H), 7.91 (d, J=8.0 Hz, 1H), 8.13 (d, J=8.8 Hz, 1H), 9.96 (d, J=8.4 Hz, 1H), 13.48 (s, 1H);

¹³C-NMR (100 MHz, CDCl₃) 44.9, 50.0, 69.4, 92.9, 98.2, 105.8, 113.5, 117.8, 126.5, 127.0, 128.8, 129.8, 130.4, 131.0, 137.3, 156.7, 157.9, 163.8, 164.8, 183.3 ppm;

GC-MS (EI): m/e 334 [M]⁺.

9,11-bis(oxiran-2-ylmethoxy)-12H-benzo[a]xanthen-12-one: m.p: 198-200° C.; Rf: 0.30 (ethyl acetate:n-hexane=1:1 (v/v));

¹H-NMR (400 MHz, CDCl₃) δ 2.80 (dd, J=4.8, 2.4 Hz, 1H), 2.96 (dd, J=4.4, 4.4 Hz, 1H), 3.00 (dd, J=4.8, 4.0 Hz, 1H), 3.15-3.17 (m, 1H), 3.38-3.42 (m, 1H), 3.52-3.55 (m, 1H), 4.02 (dd, J=10.8, 6.2 Hz, 1H), 4.20 (dd, J=11.2, 4.4 Hz, 1H), 4.36 ((dt, J=11.2, 2.4 Hz, 1H), 4.47 (dt, J=11.2, 4.2 Hz, 1H), 6.52 (d, J=2.4 Hz, 1H), 6.57 (d, J=2.4 Hz, 1H), 7.45 (d, J=8.8 Hz, 1H), 7.56 (ddd, J=7.2, 7.2, 1.2 Hz, 1H), 7.72 (ddd, J=7.2, 7.2, 1.2 Hz, 1H), 7.87 (d, J=7.2 Hz, 1H), 8.05 (d, J=8.8 Hz, 1H), 10.05 (d, J=8.8 Hz, 1H);

¹³C-NMR (100 MHz, CDCl₃) 44.8, 45.3, 50.0, 50.5, 69.5, 69.7, 94.0, 97.9, 109.8, 115.9, 117.5, 126.1, 127.3, 128.5, 129.4, 130.6, 131.3, 135.9, 156.2, 158.3, 160.8, 162.9, 177.5 ppm;

GC-MS (EI): m/e 390 [M]⁺.

EXAMPLE 18

Synthesis of 1-hydroxy-3-(thiiran-2-ylmethoxy)-12H-benzo[b]xanthen-12-one (Compound 18)

Step 1: Synthesis of 1,3-dihydroxy-12H-benzo[b]xanthen-12-one

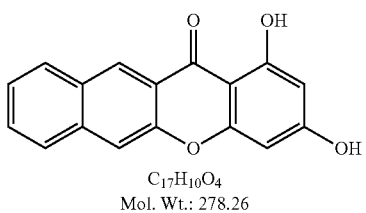 [SMILES: O=c1c2cc3ccccc3cc2oc2cc(O)cc(O)c12]

$C_{17}H_{10}O_4$
Mol. Wt.: 278.26

A mixture of 3-hydroxy-2-naphthoic acid (2.0 g, 10.63 mmol), phloroglucinol (1.34 g, 10.63 mmol), ZnCl₂ (3.30 g, 24.24 mmol) and POCl₃ (40 mL) was stirred under reflux at 80° C. for 5 hours. After the reaction was completed, the reaction mixture was cooled to room temperature and was very slowly added to 1 L of ice water. The resulting solid was allowed to stand (1 d), filtered, washed with water, and then dried under reduced pressure to obtain an ocherous compound. This compound was separated and purified by silica gel column chromatography (developing solvent: ethyl acetate:n-hexane=1:3 (v/v)) to give the title compound (289 mg, 9.8%) as a yellow solid.

Rf: 0.47 (ethyl acetate:n-hexane=1:3);

¹H-NMR (400 MHz, DMSO-d₆) δ 6.16 (s, 1H), 6.35 (s, 1H), 7.52 (dd, J=7.2, 6.8 Hz, 1H), 7.65 (dd, J=7.2, 6.8 Hz, 1H), 7.99 (s, 2H), 8.17 (d, J=8.0 Hz, 1H), 8.76 (s, 1H), 12.84 (s, 1H).

Step 2: Synthesis of 1-hydroxy-3-(thiiran-2-yl-methoxy)-12H-benzo[b]xanthen-12-one

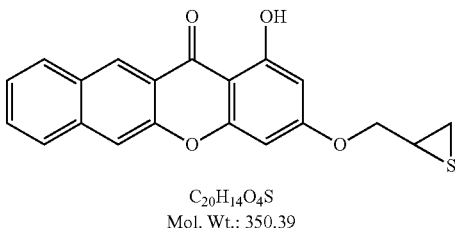

Compound 18

$C_{20}H_{14}O_4S$
Mol. Wt.: 350.39

1,3-dihydroxy-12H-benzo[b]xanthen-12-one (0.05 g, 0.18 mmol) synthesized in Step 1 of Example 18, $K_2CO_3$ (0.07 g, 0.54 mmol), and anhydrous acetone (18 mL) were charged to a dry round-bottom flask. Under stirring, epithiochlorohydrin (0.07 g, 0.72 mmol) dissolved in anhydrous acetone (2 mL) was added thereto. The reaction liquid was stirred with reflux at a temperature of 55 to 60° C. under a nitrogen atmosphere (overnight). Solid of the reaction mixture was filtered and removed, and the filtrate was concentrated under reduced pressure. The resulting residue was separated and purified by silica gel column chromatography (developing solvent: ethyl acetate:n-hexane=1:3 (v/v)) to give the title compound (13.1 mg, 20.8%) as a yellow solid.

m.p: 189-190° C.; Rf: 0.61 (ethyl acetate:n-hexane=1:3 (v/v));

$^1$H-NMR (400 MHz, CDCl$_3$) δ 2.38 (d, J=5.2 Hz, 1H), 2.67 (d, J=6.0 Hz, 1H), 3.31-3.34 (m, 1H), 4.05 (dd, J=10.4, 7.2 Hz, 1H), 4.30 (dd, J=10.4, 6.0 Hz, 1H), 6.35 (d, J=1.6 Hz, 1H), 6.47 (d, J=1.6 Hz, 1H), 7.53 (dd, J=7.6, 7.2 Hz, 1H), 7.64 (dd, J=8.0, 7.2 Hz, 1H), 7.84 (s, 1H), 7.92 (d, J=8.4 Hz, 1H), 8.06 (d, J=8.0 Hz, 1H), 8.86 (s, 1H), 12.94 (s, 1H);

$^{13}$C-NMR (100 MHz, CDCl$_3$) 24.0, 30.9, 73.2, 93.8, 96.3, 97.3, 113.5, 120.4, 126.0, 127.3, 127.9, 129.5, 129.8, 130.0, 137.0, 152.6, 158.4, 164.3, 166.0, 181.6 ppm;

EXAMPLE 19

Synthesis of 1,3-bis(thiiran-2-ylmethoxy)-12H-benzo[b]xanthen-12-1.5 one (Example 19)

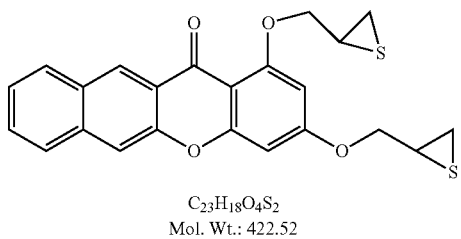

Compound 19

$C_{23}H_{18}O_4S_2$
Mol. Wt.: 422.52

1,3-dihydroxy-12H-benzo[b]xanthen-12-one (0.05 g, 0.18 mmol) synthesized in Step 1 of Example 18, $CS_2CO_3$ (0.23 g, 0.72 mmol), and anhydrous acetone (18 mL) were charged to a dry round-bottom flask, and epithiochlorohydrin (0.12 g, 1.08 mmol) dissolved in anhydrous acetone (2 mL) was added thereto with stirring. The reaction mixture was stirred with reflux under a nitrogen atmosphere (55-60° C., overnight). Solid of the reaction mixture was filtered and removed, and the filtrate was concentrated under reduced pressure. The resulting residue was separated and purified by silica gel column chromatography (developing solvent: ethyl acetate:n-hexane=1:3 (v/v)) to give the title compound (13.1 mg, 17.2%) as a yellow solid.

m.p: 196-197° C.; Rf: 0.39 (ethyl acetate:n-hexane=1:3 (v/v));

$^1$H-NMR (400 MHz, CDCl$_3$) δ 2.37 (d, J=5.2 Hz, 1H), 2.53 (d, J=4.8 Hz, 1H), 2.65 (d, J=6.0 Hz, 1H), 2.71 (d, J=6.0 Hz, 1H), 3.28-3.31 (m, 1H), 3.46-3.50 (m, 1H), 3.9), 3d, J=10.0, 7.2 Hz, 1H), 4.06 (dd, J=10.0, 7.2 Hz, 1H), 4.25 (dd, J=10.0, 5.6 Hz, 1H), 4.44 (dd, J=10.0, 4.4 Hz, 1H), 6.34 (d, J=2.4 Hz, 1H), 6.51 (d, J=2.4 Hz, 1H), 7.46 (dd, J=8.4, 7.2 Hz, 1H), 7.58 (dd, J=8.0, 7.2 Hz, 1H), 7.75 (s, 1H), 7.87 (d, J=8.0 Hz, 1H), 8.02 (d, J=8.4 Hz, 1H), 8.84 (s, 1H);

$^{13}$C-NMR (100 MHz, CDCl$_3$) 23.9, 24.6, 31.0, 31.1, 73.1, 73.8, 94.4, 96.8, 107.3, 112.8, 123.6, 125.6, 127.1, 128.4, 128.9, 130.0 (x2), 136.4, 151.7, 160.4, 161.3, 164.1, 176.2 ppm;

GC-MS (EI): m/e 422 [M]$^+$.

EXAMPLE 20

Synthesis of 1-hydroxy-3-(oxiran-2-ylmethoxy)-12H-benzo[b]xanthen-12-one

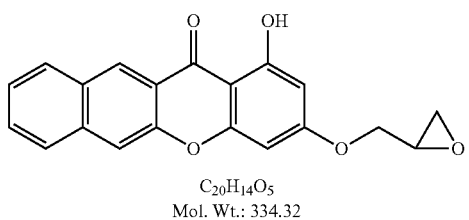 [SMILES: O=c1c2cc3ccccc3cc2oc2cc(OCC3CO3)cc(O)c12]

$C_{20}H_{14}O_5$
Mol. Wt.: 334.32

1,3-dihydroxy-12H-benzo[b]xanthen-12-one (0.1 g, 0.36 mmol) synthesized in Step 1 of Example 18, $K_2CO_3$ (0.2 g, 1.44 mmol), and DMF (5 mL) were added to a dry round-bottom flask, and epichlorohydrin (0.19 g, 2.16 mmol) was added thereto with stirring using a syringe. The reaction mixture was stirred under a nitrogen atmosphere (75° C., overnight). After the reaction was completed, water was added to the reaction mixture which was then extracted twice with ethyl acetate. The organic layer was combined, washed with brine and dried over anhydrous $Na_2SO_4$. This liquid was filtered, and the filtrate was concentrated under reduced pressure. The resulting residue was separated and purified by silica gel column chromatography (developing solvent: ethyl acetate:n-hexane=1:3 (v/v)) to give the title compound (13 mg, 10.8%) as a yellow solid.

m.p: 201-202° C.; Rf: 0.58 (ethyl acetate:n-hexane=1:1 (v/v));

$^1$H-NMR (400 MHz, CDCl$_3$) δ 2.82 (dd, J=4.4, 2.8 Hz, 1H), 2.98 (dd, J=4.4, 4.4 Hz, 1H), 3.41-3.44 (m, 1H), 4.04 (dd, J=10.8, 6.0 Hz, 1H), 4.39 (dd, J=11.2, 3.2 Hz, 1H), 6.36 (d, J=2.0 Hz, 1H), 6.50 (d, J=2.0 Hz, 1H), 7.52 (dd, J=7.2, 6.8 Hz, 1H), 7.64 (dd, J=7.2, 6.8 Hz, 1H), 7.84 (s, 1H), 7.92 (d, J=8.4 Hz, 1H), 8.07 (d, J=8.4 Hz, 1H), 8.85 (s, 1H);

$^{13}$C-NMR (100 MHz, CDCl$_3$+CD$_3$OD) 44.8, 50.0, 69.4, 94.0, 97.2, 113.4, 113.5, 120.3, 126.0, 127.3, 127.8, 129.6, 129.8, 129.9, 137.0, 152.1, 158.4, 163.9, 166.1, 181.7 ppm; GC-MS (EI): m/e 334 [M]$^+$.

EXAMPLE 21

Synthesis of 1,3-bis(oxiran-2-ylmethoxy)-12H-benzo[b]xanthen-12-one (Compound 20)

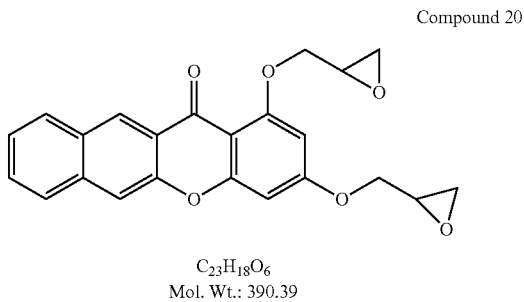 [SMILES: O=c1c2cc3ccccc3cc2oc2cc(OCC3CO3)cc(OCC3CO3)c12]

Compound 20

C$_{23}$H$_{18}$O$_6$
Mol. Wt.: 390.39

1,3-dihydroxy-12H-benzo[b]xanthen-12-one (0.15 g, 0.54 mmol) synthesized in Step 1 of Example 18, CS$_2$CO$_3$ (0.53 g, 1.62 mmol), and anhydrous acetone (30 mL) were charged to a dry round-bottom flask, and epichlorohydrin (0.25 g, 2.7 mmol) was added thereto with stirring using a syringe. The reaction mixture was stirred with reflux under a nitrogen atmosphere (55 to 60° C., overnight). Solid of the reaction mixture was filtered and removed, and the filtrate was concentrated under reduced pressure. The resulting residue was separated and purified by silica gel column chromatography (developing solvent: ethyl acetate:n-hexane=1:3 (v/v)) to give the title compound (15.3 mg, 21.8%) as a yellow solid.

m.p.: 181-182° C.; Rf: 0.26 (ethyl acetate:n-hexane=1:1 (v/v));

$^1$H-NMR (400 MHz, CDCl$_3$) δ 2.80 (dd, J=4.8, 2.4 Hz, 1H), 2.96 (dd, J=4.0, 2.4 Hz, 1H), 2.99 (dd, J=5.2, 4.4 Hz, 1H), 3.21-3.25 (m, 1H), 3.35-3.41 (m, 1H), 3.47-3.52 (m, 1H), 4.00 (ddd, J=10.4, 5.2, 2.0 Hz, 1H), 4.18 (dd, J=11.2, 4.4 Hz, 1H), 4.36 (dt, J=9.6, 2.4 Hz, 1H), 4.40 (dt, J=11.2, 2.4 Hz, 1H), 6.37 (d, J=2.4 Hz, 1H), 6.49 (d, J=2.4 Hz, 1H), 7.45 (ddd, J=8.0, 6.8, 1.2 Hz, 1H), 7.56 (ddd, J=8.0, 6.8, 1.2 Hz, 1H), 7.72 (s, 1H), 7.85 (d, J=8.0 Hz, 1H), 8.01 (d, J=8.4 Hz, 1H), 8.82 (s, 1H);

$^{13}$C-NMR (100 MHz, CDCl$_3$) 44.8, 45.2, 50.0, 50.3, 69.0, 69.5, 94.5, 96.6, 107.3, 112.8, 122.7, 125.5, 127.1, 128.3, 128.9, 130.0 (x2), 136.3, 151.7, 160.3, 161.2, 164.1, 175.9 ppm;

GC-MS (EI): m/e 390 [M]$^+$.

EXPERIMENTAL EXAMPLE 1

Anticancer Sensitization Test

In order to investigate effects of compounds in accordance with the present invention on the activity of P-gp, cytotoxicity, and anticancer drug accumulation and efflux experiments were performed in a human breast cancer cell line (MCF-7/ADR) having resistance to various anticancer drugs due to the overexpression of P-gp (Skehan et al., *J. Natl. Cancer. Inst.*, 82, pp 1107-1112, 1990; Critchfield et al., *Biochem. Pharmacol.*, 48, pp 1437-1445, 1994; Harker et al., *Cancer Res.*, 45, pp 4091-4096, 1985; Yeh et al., *Cancer Res.*, 52, pp 6692-6695, 1992; Zhang et al., *J. Pharmacol. Exp. Ther.*, 304, pp 1258-1267, 2004; Chung et al., *Phytother Res*, 21, pp 565-569, 2007; and Chung et al., *Phytother Res*, 23, pp 472-476, 2009).

1-1. Reagents and Equipment

A cell culture medium RPMI 1640, trypsin-EDTA (0.25% trypsin-1 mM EDTA) and Antibiotic-antimycotic reagent were purchased from Invitrogen (Calsbad, USA); and fetal bovine serum (FBS) was purchased from Hyclone (South Logan, USA). Daunomycin (DNM), verapamil, DMSO, sulforhodamine B (SRB), sodium hydrogen carbonate, L-glutamine, trichloroacetic acid (TCA), NaCl, KCl, and MgCl$_2$ were purchased from Sigma-Aldrich (St. Louis, USA). CaCl$_2$ was purchased from Showa Chemical (Tokyo, Japan), and acetic acid was purchased from Daejung (Siheung, Korea). HEPES (N-(2-hydroxyethyl)piperazine-N'-2-ethanesulfonic acid), Triton X-100 and Tris base were purchased from USB (Cleveland, USA). Microscint (Microscint TM40, scintillation cocktail) was purchased from Packard Instrument Co., Inc. (Meriden, USA), [$^3$H]-DNM (1-5 Ci/mmol) was purchased from Perkin-Elmer Inc. (Wellesley, USA). 6-well plates and 96-well plates were purchased from BD Biosciences (Bedford, USA). As experimental equipment, a cell culture incubator (3158 Form a Scientific Inc., Marietta, USA), a scintillation and luminescence counter (Topcount NXT, Packard Instrument Co., Inc., Meriden USA), an orbital shaker (SLOSb20, SLB, Seoul, Korea), an inverted microscope (Axiovert 200, Carl Zeiss, Oberkochen, Germany), and an ELISA reader (3550, Bio-Rad, Hercules, USA) were used.

1-2. Cell Culture Conditions

MCF-7/ADR cells, which is a human breast cancer cell line with multidrug resistance (P-gp overexpressing cell), were cultured in an RPMI 1640 medium containing 10% FBS, 10 mM HEPES, 24 mM sodium hydrogen carbonate, 2 mM L-glutamine and an antibiotic, in a cell culture incubator at 37° C. under a supply of 5% CO$_2$ and 95% air.

1-3. Effects of Compounds on Cytotoxicity

MCF-7/ADR cells were seeded onto a 96-well plate at a density of 5×10$^3$ cells/well. The cells were cultured to confluence on the plate at 37° C. for 24 hours.

1.25×10$^{-6}$ M to 7.5×10$^{-5}$ M of daunomycin (DNM), 100 μM of a representative P-gp inhibitor, verapamil (positive control) and samples including the compounds of the present invention were added to each well. At this time, the group to which only DMSO was added in place of the compounds in accordance with the present invention was taken as a control. After 2 hours, the culture fluid (daunomycin±the compounds of the present invention or verapamil) was removed, cells were washed twice with RPMI 1640, and a fresh medium was added. After 3 days, cytotoxicity was examined according to an SRB staining method which is briefly described as follows. Cells were fixed with 10% TCA for one hour, washed 4 times with water, and then dried. An SRB reagent (0.4% w/v in 1% acetic acid) was added to each well and one hour later, the plate was washed 4 times with 1% acetic acid. The plate was dried, a dye bound to the protein was dissolved in 10 mM Tris base for one hour, an absorbance at 570 nm was measured, and then an IC$_{50}$ value was calculated. The IC$_{50}$ value refers to a concentration of a drug B which is capable of providing a 50% decrease in the magnitude of a reaction A, assuming that the magnitude of the reaction A is taken to be 100%.

According to the experimental results, as shown in Table 1 below, the compounds or the present invention lowered an IC$_{50}$ value of daunomycin in MCF-7/ADR cells, comparably to verapamil known as a representative P-gp inhibitor.

Accordingly, it is considered that the compounds of the present invention have a possibility of development as a P-gp inhibitor.

TABLE 1

IC$_{50}$ value of daunomycin after 2-hour incubation of daunomycin and samples

| Samples | IC$_{50}$ value of daunomycin (μM) |
|---|---|
| DNM (Control) | 25.64 |
| DNM + Verapamil (Positive control) | 3.54 |
| DNM + Compound 1 | 47.86 |
| DNM + Compound 2 | 3.04 |
| DNM + Compound 3 | 6.47 |
| DNM + Compound 4 | 6.47 |
| DNM + Compound 5 | 5.26 |
| DNM + Compound 6 | 19.95 |
| DNM + Compound 7 | 23.92 |
| DNM + Compound 8 | 34.20 |
| DNM + Compound 9 | 5.65 |
| DNM + Compound 10 | 4.04 |
| DNM + Compound 11 | 39.51 |
| DNM + Compound 12 | 11.17 |
| DNM + Compound 13 | 14.72 |
| DNM + Compound 14 | 18.03 |
| DNM + Compound 15 | 8.99 |
| DNM + Compound 16 | 19.68 |
| DNM + Compound 17 | 7.05 |
| DNM + Compound 18 | 15.37 |
| DNM + Compound 19 | 5.98 |
| DNM + Compound 20 | 4.11 |

1-4. Effects of Compounds on Intracellular Accumulation of [$^3$H]-Daunomycin

In order to investigate effects of the compounds of the present invention on the activity of P-gp, MCF-7/ADR cells were seeded onto a 6-well plate at a density of 1.5×10$^5$ cells/well, followed by culturing for 72 hours. Then, 100 μM of verapamil or the compounds of the present invention which decided to have feasibility as a P-gp inhibitor in a cytotoxicity test, and 1 mL of an uptake buffer (137 mM NaCl, 5.4 mM KCl, 2.8 mM CaCl$_2$, 1.2 mM MgCl$_2$, 10 mM HEPES, pH 7.4) containing 0.05 μM of [$^3$H]-daunomycin were added to each well, followed by culturing for 2 hours. Then, the uptake buffer of each well was removed, and an ice-cold stop solution (137 mM NaCl, 14 mM Tris, pH 7.4) was added to terminate the accumulation of [$^3$H]-daunomycin. 1 mL of a lysis buffer (1% Triton X-100) was added to each well, followed by shaking at 150 rpm for one hour, and 100 μL was aliquoted and subjected to counting of radioactivity using a liquid scintillation counter (LSC).

The intracellular accumulation results of the control group and the intracellular accumulation results obtained after treatment of cells with the compounds of the present invention were subjected to a statistical analysis according to a student's t-test. When a p value is less than 0.05 (p<0.05), a decision was made as being statistically significant. The results are given in Table 2 below.

TABLE 2

Intracellular accumulation amount of daunomycin (%) after 2-hour incubation of daunomycin and samples

| Samples | Intracellular accumulation amount of daunomycin (%) |
|---|---|
| DNM (Control) | 100 |
| DNM + Verapamil (Positive control) | 319 ± 12.54** |
| DNM + Compound 2 | 434 ± 27.93** |
| DNM + Compound 7 | 337 ± 8.17** |

TABLE 2-continued

Intracellular accumulation amount of daunomycin (%) after 2-hour incubation of daunomycin and samples

| Samples | Intracellular accumulation amount of daunomycin (%) |
|---|---|
| DNM + Compound 9 | 239 ± 33.73** |
| DNM + Compound 10 | 707 ± 50.96** |
| DNM + Compound 12 | 651 ± 34.34** |
| DNM + Compound 13 | 247 ± 20.21** |
| DNM + Compound 14 | 189 ± 43.66* |
| DNM + Compound 15 | 529 ± 140.63** |
| DNM + Compound 17 | 346 ± 52.83** |
| DNM + Compound 18 | 211 ± 110.89 |
| DNM + Compound 19 | 697 ± 163.02** |

(In the above Table, individual data are expressed in mean ± S.D. (n = 3-4), *represents p value<0.01, and **represents p value<0.005)

1-5. Effects of Inventive Compounds on Cellular Efflux of [$^3$H]-Daunomycin

In order to re-confirm that increased accumulation of daunomycin in human breast cancer cells is due to inventive compound-induced inhibition of efflux of daunomycin introduced into cells, effects of the inventive compounds on the cellular efflux of daunomycin were examined according to the following experimental procedure.

MCF-7/ADR cells were seeded onto a 6-well plate at a density of 1.5×10$^5$ cells/well and cultured for 72 hours. 1 mL of an uptake buffer containing 0.05 μM of [$^3$H]-daunomycin was added to each well, and the cells were cultured at 37° C. for one hour to result in intracellular accumulation of daunomycin. Thereafter, the uptake buffer containing [$^3$H]-daunomycin was removed and the cells were washed. Then, 100 μM of verapamil or an uptake buffer containing the compounds of the present invention decided to have feasibility as a P-gp inhibitor in a cytotoxicity test were added to each well, followed by culturing for one hour. On the other hand, the control group was treated with a drug-free uptake buffer. After one hour, the cells were washed twice with an ice-cold stop solution, 1 mL of a lysis buffer was added to each well, followed by shaking at 150 rpm for one hour, and 100 μL was aliquoted and subjected to counting of radioactivity using a liquid scintillation counter (LSC). At this time, since the measured value corresponds to the remaining amount of daunomycin in cells, the cellular efflux amount of [$^3$H]-daunomycin for one hour was calculated by subtracting the remaining amount of daunomycin in cells after culturing of cells with the compounds of the present invention for one hour from the intracellular influx amount of daunomycin (total amount) immediately after culturing of cells with 0.05 μM of [$^3$H]-daunomycin. The results are given in Table 3 below.

TABLE 3

Cellular efflux amount of daunomycin (%) after incubation of intracellularly accumulated daunomycin with samples for one hour

| Samples | Cellular efflux amount of daunomycin (%) |
|---|---|
| DNM (Control) | 72.79 ± 3.43 |
| DNM + Verapamil (Positive control) | 51.25 ± 3.21** |
| DNM + Compound 1 | 62.87 ± 3.13* |
| DNM + Compound 2 | 44.88 ± 8.52** |
| DNM + Compound 7 | 44.55 ± 6.76** |
| DNM + Compound 9 | 49.54 ± 5.34** |
| DNM + Compound 10 | 47.87 ± 5.87** |
| DNM + Compound 12 | 40.39 ± 4.38** |
| DNM + Compound 13 | 44.58 ± 8.44** |

TABLE 3-continued

Cellular efflux amount of daunomycin (%) after incubation of intracellularly accumulated daunomycin with samples for one hour

| Samples | Cellular efflux amount of daunomycin (%) |
|---|---|
| DNM + Compound 14 | 64.81 ± 20.45 |
| DNM + Compound 15 | 40.04 ± 5.33** |
| DNM + Compound 17 | 51.74 ± 5.80** |
| DNM + Compound 18 | 44.15 ± 5.08** |
| DNM + Compound 19 | 42.45 ± 7.23** |

(In the above Table, individual data are expressed in mean ± S.D. (n = 3-4), *represents p value<0.01, and **represents p value<0.005)

From the above experimental results, it can be seen that the inventive compounds exhibit a P-gp activity inhibitory action equal to or superior to that of verapamil known as a currently representative P-gp inhibitor.

INDUSTRIAL APPLICABILITY

As described above, xanthone derivative compounds of the present invention or pharmaceutically acceptable salts thereof. Can inhibit the activity of the P-glycoprotein (P-gp) to prevent cellular efflux of an anticancer drug such that accumulation of the anticancer drug in cancer cells is increased to result in effective death of cancer cells and inhibition of cancer growth. Therefore, the compounds of the present invention may be usefully used as an anticancer-aiding composition for the prevention or treatment of cancer diseases.

What is claimed is:

1. A method for reducing resistance of a subject to an anticancer drug, comprising administering at least one of a compound represented by formula I or a pharmaceutically acceptable salt thereof:

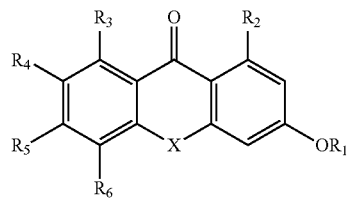

[Formula I]

wherein X represents —S— or —O—;

$R_1$ represents —CH$_2$—CH(OH)—CH$_2$Cl, —CH$_2$—CH(OH)—CH$_2$OH, —CH$_2$—CH(SH)—CH$_2$Cl, —CH$_2$—CH(SH)—CH$_2$OH,

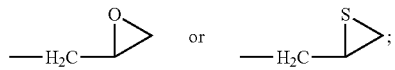

$R_2$ represents hydrogen, —OH, (C$_1$-C$_4$)alkoxy,

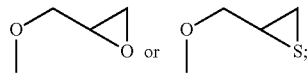

and $R_3$, $R_4$, $R_5$, and $R_6$ each independently represent H or (C$_1$-C$_4$)alkoxy, or alternatively $R_3$ and $R_4$, $R_4$ and $R_5$, or $R_5$ and $R_6$ represent —CH=CH—CH=CH—.

* * * * *